US011448586B2

(12) United States Patent
Takashima et al.

(10) Patent No.: US 11,448,586 B2
(45) Date of Patent: Sep. 20, 2022

(54) INSPECTION APPARATUS, SENSING APPARATUS, SENSITIVITY CONTROL APPARATUS, INSPECTION METHOD, AND PROGRAM WITH PIXEL SENSITIVITY CONTROL

(71) Applicant: Sony Group Corporation, Tokyo (JP)

(72) Inventors: Masatoshi Takashima, Tokyo (JP); Yoshihiro Murakami, Kanagawa (JP); Hiroshi Mori, Kanagawa (JP)

(73) Assignee: Sony Group Corporation, Tokyo (JP)

( * ) Notice: Subject to any disclaimer, the term of this patent is extended or adjusted under 35 U.S.C. 154(b) by 0 days.

(21) Appl. No.: 15/575,529

(22) PCT Filed: Jun. 10, 2016

(86) PCT No.: PCT/JP2016/067321
§ 371 (c)(1),
(2) Date: Nov. 20, 2017

(87) PCT Pub. No.: WO2016/208415
PCT Pub. Date: Dec. 29, 2016

(65) Prior Publication Data
US 2018/0136116 A1 May 17, 2018

(30) Foreign Application Priority Data
Jun. 26, 2015 (JP) .............................. JP2015-128878

(51) Int. Cl.
*G01N 21/25* (2006.01)
*A01G 7/00* (2006.01)
(Continued)

(52) U.S. Cl.
CPC ............. *G01N 21/255* (2013.01); *A01G 7/00* (2013.01); *G01J 1/4204* (2013.01);
(Continued)

(58) Field of Classification Search
CPC .. G01N 21/255; G01N 33/0098; G01N 21/27; G01N 2201/0616; A01G 7/00; G01J 3/51
See application file for complete search history.

(56) References Cited

U.S. PATENT DOCUMENTS

| 2001/0016053 A1 | 8/2001 | Hendrickson et al. |
| 2002/0105581 A1* | 8/2002 | Masaki ............. H04N 5/23225 348/229.1 |

(Continued)

FOREIGN PATENT DOCUMENTS

| CN | 1286898 A | 3/2001 |
| JP | 52-000392 B | 1/1997 |

(Continued)

OTHER PUBLICATIONS

Chinese Office Action dated Sep. 2, 2020 for corresponding Chinese Application No. 201680035821.6.

(Continued)

*Primary Examiner* — Hwa Andrew Lee
(74) *Attorney, Agent, or Firm* — Michael Best & Friedrich LLP

(57) ABSTRACT

The present disclosure relates to an inspection apparatus, a sensing apparatus, a sensitivity control apparatus, an inspection method, and a program that perform inspection with improved accuracy. The inspection apparatus includes a detection section for detecting a plurality of different wavelength region components of ambient light reflected from an inspection target to be inspected, and a control section for controlling the sensitivity of each of the different wavelength region components. The control section controls the sensitivity by calculating a histogram indicating the detection level in every wavelength region of light reflected from the inspection target that is detected by the detection section, and determining, based on histograms of particular spectroscopic components, whether or not the sensitivity is properly (Continued)

set for the detection section. The present technology is applicable, for example, to an inspection apparatus that inspects vegetation.

16 Claims, 24 Drawing Sheets

(51) Int. Cl.
*G01N 21/27* (2006.01)
*G01J 3/28* (2006.01)
*G01J 1/42* (2006.01)
*G01J 3/02* (2006.01)
*G01J 3/42* (2006.01)
*G01N 33/00* (2006.01)
*G01N 21/84* (2006.01)
*G01J 3/18* (2006.01)

(52) U.S. Cl.
CPC ........... *G01J 3/0208* (2013.01); *G01J 3/0224* (2013.01); *G01J 3/2803* (2013.01); *G01J 3/42* (2013.01); *G01N 21/27* (2013.01); *G01N 21/274* (2013.01); *G01N 33/0098* (2013.01); *G01J 3/18* (2013.01); *G01J 2003/2806* (2013.01); *G01J 2003/425* (2013.01); *G01N 2021/8466* (2013.01); *G01N 2201/0616* (2013.01)

(56) References Cited

U.S. PATENT DOCUMENTS

| | | | |
|---|---|---|---|
| 2009/0309960 | A1 | 12/2009 | Park et al. |
| 2010/0321522 | A1 | 12/2010 | Seto |

FOREIGN PATENT DOCUMENTS

| | | | | |
|---|---|---|---|---|
| JP | 2003-009664 | A | | 1/2003 |
| JP | 2003-214951 | A | | 7/2003 |
| JP | 2003214951 | A | * | 7/2003 |
| JP | 2004-157062 | A | | 6/2004 |
| JP | 2007-127657 | A | | 5/2007 |
| JP | 2007127657 | A | | 5/2007 |
| JP | 2011-004257 | A | | 1/2011 |
| JP | 2013231645 | A | * | 11/2013 |
| JP | 2014-132256 | A | | 7/2014 |
| JP | 2014-183788 | A | | 10/2014 |
| WO | 2009/018582 | A2 | | 2/2009 |
| WO | WO-2009/018582 | A2 | | 2/2009 |
| WO | WO-2014/156039 | A1 | | 10/2014 |

OTHER PUBLICATIONS

Extended European Search Report dated Oct. 31, 2018 for corresponding European Application No. 16814186.9.
Chinese Office Action dated Nov. 13, 2019 for corresponding Chinese Application No. 201680035821.6.

* cited by examiner

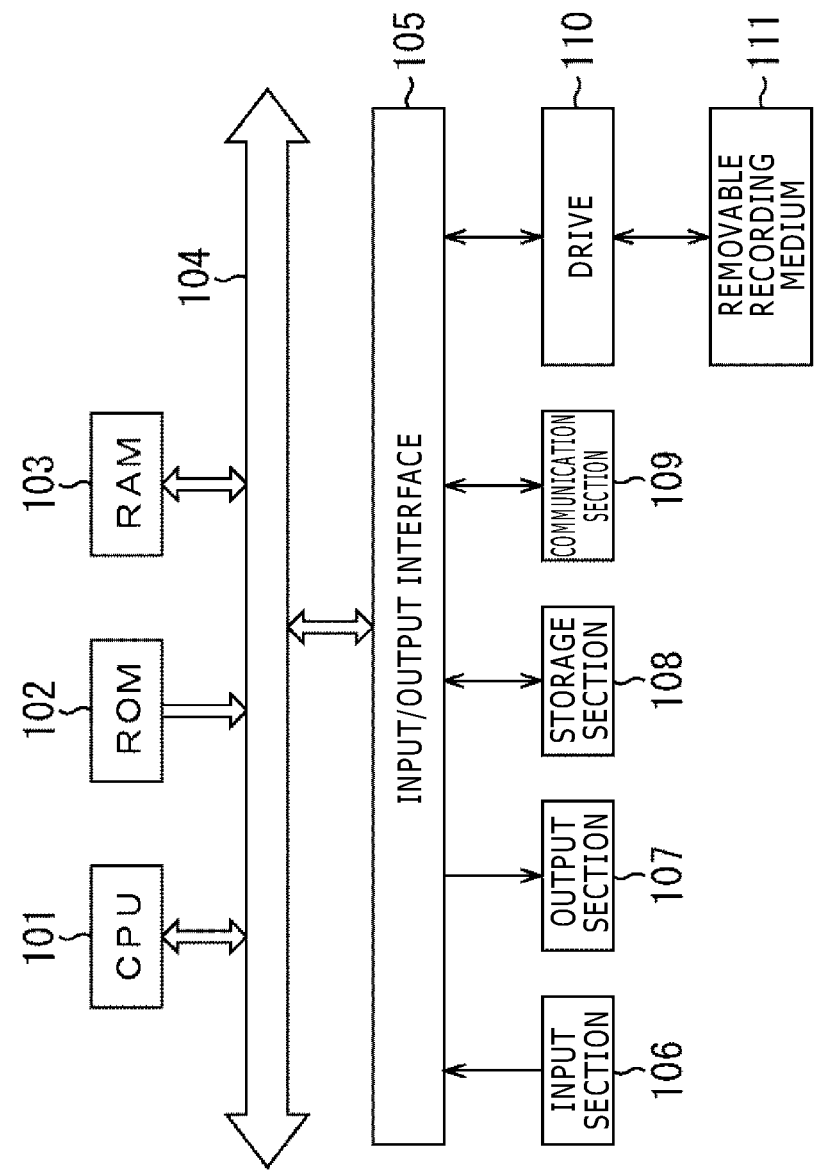

INSPECTION APPARATUS, SENSING APPARATUS, SENSITIVITY CONTROL APPARATUS, INSPECTION METHOD, AND PROGRAM WITH PIXEL SENSITIVITY CONTROL

TECHNICAL FIELD

The present disclosure relates to an inspection apparatus, a sensing apparatus, a sensitivity control apparatus, an inspection method, and a program, and more particularly, to an inspection apparatus, a sensing apparatus, a sensitivity control apparatus, an inspection method, and a program that perform inspection with improved accuracy.

BACKGROUND ART

A conventionally known inspection apparatus (refer, for example, to PTL 1) inspects vegetation, that is, the state and activity of plants growing in a certain place.

CITATION LIST

Patent Literature

[PTL 1]
JP 2003-9664A

SUMMARY

Technical Problem

However, it is demanded that inspection be performed with higher accuracy than the above-described inspection apparatus.

The present disclosure has been made in view of the above circumstances in order to perform inspection with higher accuracy.

Solution to Problem

According to an aspect of the present disclosure, there is provided an inspection apparatus including a detection section and a control section. The detection section detects a plurality of different wavelength region components of ambient light that is reflected from an inspection target to be inspected. The control section controls the sensitivity of each of the plurality of different wavelength region components.

According to another aspect of the present disclosure, there is provided a sensing apparatus including a sensing element and a control section. The sensing element uses each of planarly arrayed pixels to detect a plurality of different wavelength region components of ambient light that is reflected from an inspection target to be inspected. The control section controls the sensitivity of each of the different wavelength region components.

According to yet another aspect of the present disclosure, there is provided a sensitivity control apparatus including a control section. The control section controls the sensitivity of each of a plurality of different wavelength region components of ambient light that is reflected from an inspection target to be inspected.

According to still another aspect of the present disclosure, there is provided an inspection method including detecting a plurality of different wavelength region components of ambient light that is reflected from an inspection target to be inspected, and controlling the sensitivity of each of the different wavelength region components.

According to an additional aspect of the present disclosure, there is provided a program causing a computer to function as a control section configured to control the sensitivity of each of a plurality of different wavelength region components of ambient light that is reflected from an inspection target to be inspected.

An aspect of the present disclosure detects a plurality of different wavelength region components of ambient light that is reflected from an inspection target to be inspected, and controls the sensitivity of each of the different wavelength region components.

Advantageous Effect of Invention

An aspect of the present disclosure makes it possible to perform inspection with higher accuracy.

BRIEF DESCRIPTION OF DRAWINGS

FIG. 26 is a block diagram illustrating an exemplary configuration of an embodiment of a computer to which the present technology is applied.

DESCRIPTION OF EMBODIMENTS

Embodiments to which the present technology is applied will now be described in detail with reference to the accompanying drawings.

First Embodiment of Vegetation Inspection Apparatus

Figure 1:
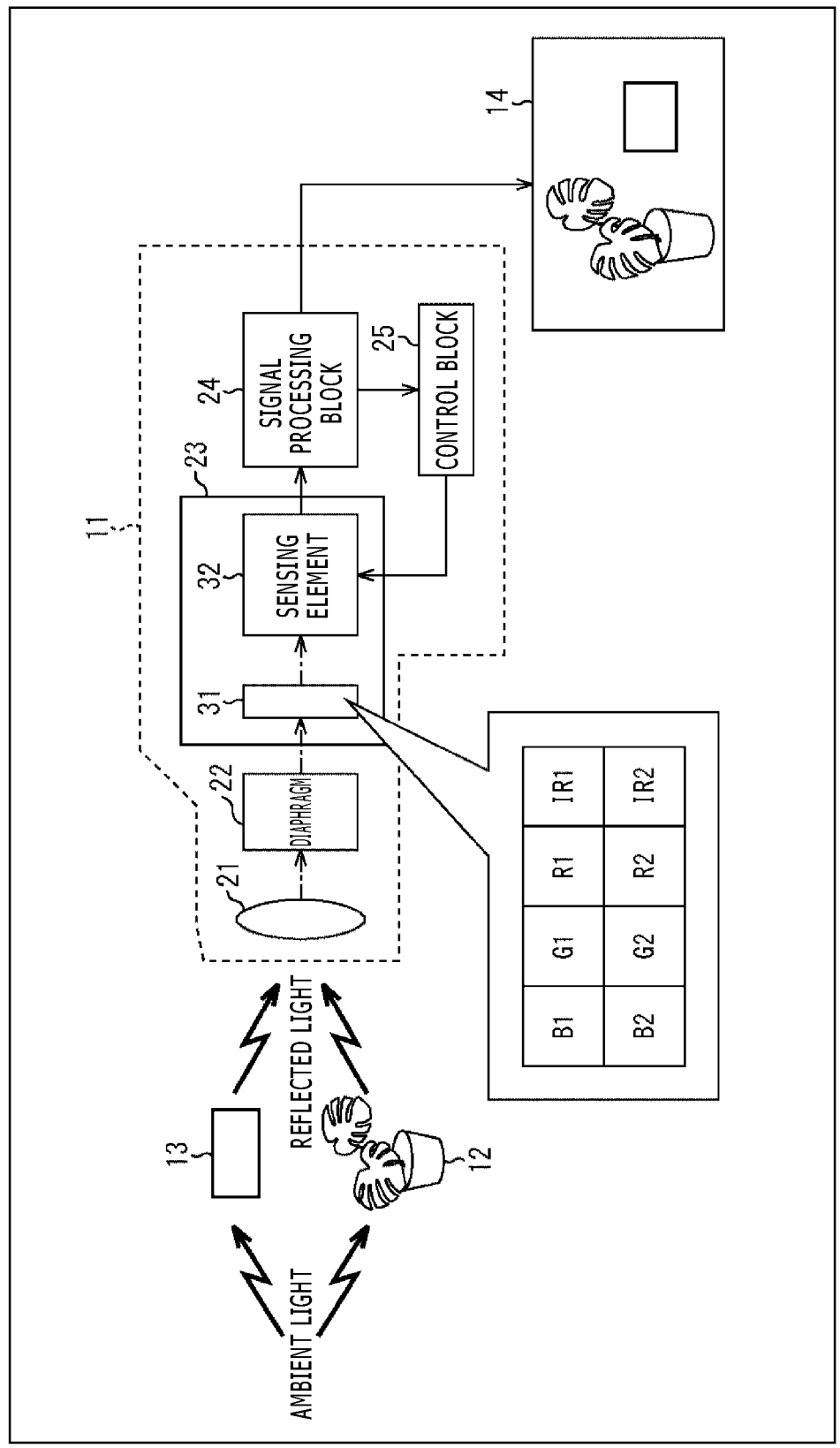
FIG. 1 is a block diagram illustrating an exemplary configuration of a first embodiment of a vegetation inspection apparatus to which the present technology is applied.

FIG. 1 is a block diagram illustrating an exemplary configuration of a first embodiment of a vegetation inspection apparatus to which the present technology is applied.

As illustrated in FIG. 1, for example, sunlight or other ambient light reflected from an inspection target 12 and a reference reflective plate 13 is incident on the vegetation inspection apparatus 11. The vegetation inspection apparatus 11 outputs to a display section 14, for example, an image or other sensing result that is obtained by sensing the inspection target 12 and the reference reflective plate 13.

Further, the vegetation inspection apparatus 11 is capable of sensing, for example, lawn or other plant as the inspection target 12 and calculating a normalized difference vegetation index NDVI, which is an index indicative, for example, of the distribution or activity of vegetation. In this instance, the vegetation inspection apparatus 11 eliminates the spectroscopic properties of the ambient light from the light reflected from the inspection target 12 by reference to the light reflected from the reference reflective plate 13 having known reflectance properties. The vegetation inspection apparatus 11 is then able to generate an NDVI image in compliance with the normalized difference vegetation index NDVI and display the generated NDVI image on the display section 14.

The vegetation inspection apparatus 11 includes, for example, an optical system 21, a diaphragm 22, a spectral sensor 23, a signal processing block 24, and a control block 25. The spectral sensor 23 includes a spectroscope 31 and a sensing element 32.

The optical system 21 includes one or more lenses, collects light reflected from the inspection target 12 and the reference reflective plate 13, which is incident on the vegetation inspection apparatus 11, and forms an image on the detection plane of the sensing element 32 in the spectral sensor 23.

The diaphragm 22 controls the amount of light to be collected by the spectral sensor 23 through the optical system 21 in order to adjust the exposure of the image to be sensed by the vegetation inspection apparatus 11.

The spectral sensor 23 detects a plurality of different wavelength region components of ambient light reflected from the inspection target 12 and the reference reflective plate 13. More specifically, the spectral sensor 23 uses the spectroscope 31 to disperse the reflected light into a plurality of different wavelength regions of light, uses the individual pixels of the sensing element 32 to detect the brightness of each of the different wavelength regions of light (spectroscopic components), and supplies the resulting detection signal to the signal processing block 24.

The spectroscope 31 includes a plurality of optical filters that transmit a predetermined wavelength region of light. The respective optical filters are disposed on the respective pixels of the sensing element 32 to disperse the light incident on the detection plane of the sensing element 32.

As illustrated, the spectroscope 31 is configured so that, for example, eight different optical filters for transmitting respective different wavelength regions of light are disposed corresponding to eight pixels forming one set of two vertically arrayed pixels by four horizontally arrayed pixels. More specifically, the optical filters disposed corresponding to a set of eight pixels are, in order from the shortest wavelength to the longest, the optical filter for transmitting first blue light B1, the optical filter for transmitting second blue light B2, the optical filter for transmitting first green light G1, the optical filter for transmitting second green light G2, the optical filter for transmitting first red light R1, the optical filter for transmitting second red light R2, the optical filter for transmitting first infrared light IR1, and the optical filter for transmitting second infrared light IR2.

The spectroscope 31 is configured so that one set is formed of 8-pixel optical filters, and that n sets of such optical filters (where n is a natural number of 1 or greater) are successively disposed on the whole detection plane of the sensing element 32. One set of the optical filters is not limited to a set of eight pixels. An alternative configuration may be employed so that one set of the optical filter is formed, for example, of four pixels.

The sensing element 32 may be formed, for example, of an imaging element that is configured by arranging a plurality of pixels in a matrix form and disposing them on the detection plane. The sensing element 32 detects the brightness of spectroscopic components dispersed by each optical filter of the spectroscope 31 on an individual pixel basis and outputs a detection signal based on the brightness of each spectroscopic component.

The sensing element 32 may be formed of an area sensor or a line sensor. The area sensor detects an area of a target. The line sensor detects a line of the target. Further, even in a case where the sensing element 32 is formed of only one R-component pixel and one IR-component pixel, the target can be scanned by providing a mechanism for moving a sensor or a measurement target.

The signal processing block 24 processes the detection signal outputted from the spectral sensor 23 to build an image, and outputs the image to the display section 14 as the sensing result. Further, in order to calculate a proper normalized difference vegetation index NDVI, the signal processing block 24 sets the sensitivity of pixels in the sensing element 32 for each spectroscopic component dispersed by the spectroscope 31, as described later with reference to FIGS. 7 to 9, and notifies the control block 25 of an exposure time based on the sensitivity setting. Moreover, as described later with reference to FIG. 10, the signal processing block 24 performs a gain calibration process at the time of calculating the normalized difference vegetation index NDVI.

In order to expose the pixels for the exposure time designated by the signal processing block 24, the control block 25 controls the exposure time for each pixel receiving the same spectroscopic component.

The vegetation inspection apparatus 11 configured as described above is capable of calculating a proper normalized difference vegetation index NDVI on a basis of light reflected from the inspection target 12 by performing a sensitivity setup process and gain calibration process in the signal processing block 24.

Spectral properties prevailing in a case where lawn is the inspection target 12 will now be described with reference to FIG. 2.

Figure 2:
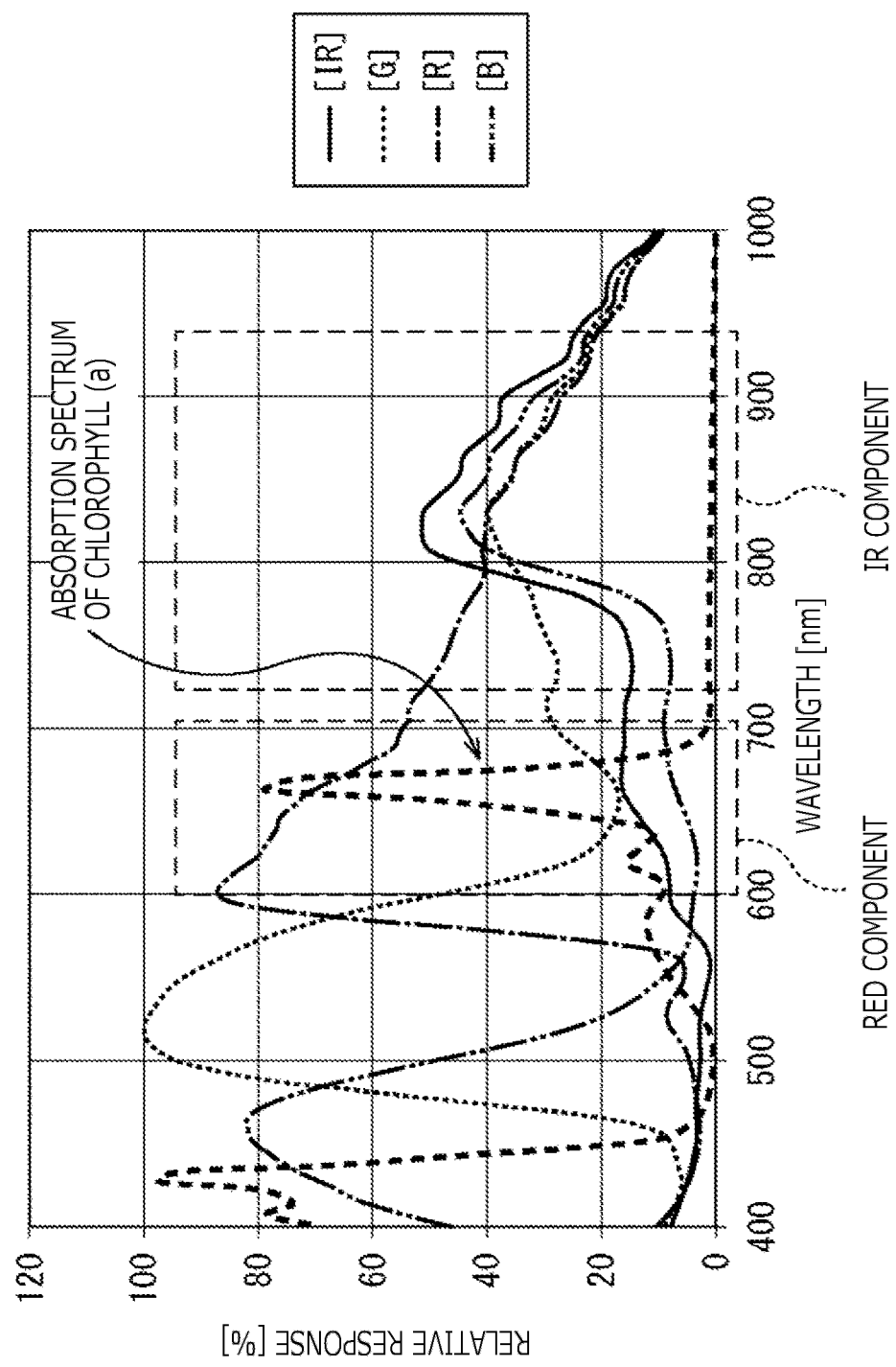
FIG. 2 is a diagram illustrating spectral properties that prevail in a case where lawn is an inspection target.

FIG. 2 illustrates the relationship between the sensor sensitivity of the sensing element 32 and the absorption spectrum of chlorophyll. The horizontal axis represents wavelength, and the vertical axis represents relative sensitivity.

As illustrated in FIG. 2, the relative sensitivity settings of the sensing element 32 for infrared light IR, green light G, red light r, and blue light B are high in the respective wavelength regions of light. More specifically, the sensing element 32 is set so that the relative sensitivity setting for pixels detecting red light R is high within a wavelength region of approximately 600 to 700 nm, and that the relative sensitivity setting for pixels detecting infrared light IR is high within a wavelength region of approximately 720 to 940 nm.

Further, as illustrated in FIG. 2, chlorophyll included in the lawn has absorption properties that absorb the greatest amount of light at a wavelength of approximately 660 nm. That is to say, chlorophyll is such that the absorption of light reaches a peak in the wavelength region of red light R and does not substantially occur in the wavelength region of infrared light IR.

A vegetation index to be used as an inspection value for vegetation inspection can be calculated on the basis of the above-described absorption properties of chlorophyll. For example, the normalized difference vegetation index NDVI is calculated from Equation (1) below by using the pixel value of red light R and the pixel value of infrared light IR (near-infrared region component).

[Mathematical 1]

$$NDVI = \frac{IR - R}{IR + R} \tag{1}$$

The present embodiment is described in relation to the use of the normalized difference vegetation index NDVI. However, the vegetation inspection apparatus 11 may use a vegetation index other than the normalized difference vegetation index NDVI, such as a ratio vegetation index (RVI) or a green NDVI (GNDVI), for example.

Figure 3:
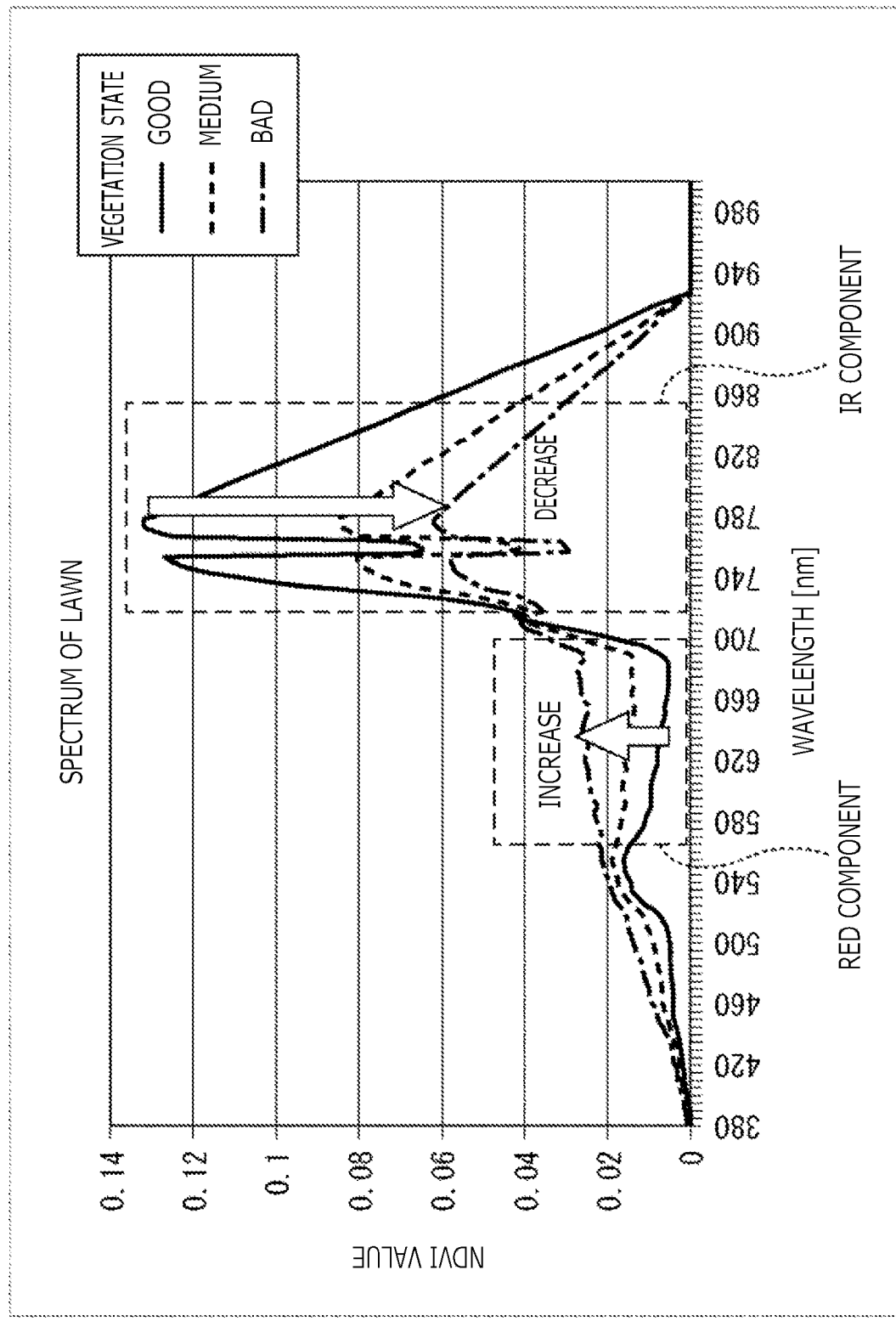
FIG. 3 is a diagram illustrating a spectrum of lawn.

Referring now to FIG. 3, the relationship between the vegetation state of lawn and the normalized difference vegetation index NDVI will now be described.

FIG. 3 illustrates the spectrum of lawn that is used as the inspection target 12. The horizontal axis represents wavelength, and the vertical axis represents the normalized difference vegetation index NDVI.

In a case where, for example, the lawn is in a good vegetation state, red light R is significantly absorbed by the lawn. In this instance, therefore, the reflected light contains a small amount of red light R and a large amount of infrared light IR. Thus, the normalized difference vegetation index NDVI exhibits a high value. Meanwhile, when the vegetation state of the law degrades, the lawn absorbs a decreased amount of red light R. Therefore, the reflected light contains an increased amount of red light R and a decreased amount of infrared light IR. Thus, the normalized difference vegetation index NDVI exhibits a low value.

As described above, the vegetation inspection apparatus 11 is capable of inspecting the vegetation state of the lawn by determining the normalized difference vegetation index NDVI. The vegetation inspection apparatus 11 can be used, for example, to inspect the vegetation state of a lawn stadium where soccer or other sport is played.

Example of Lawn Stadium Inspection

An example of inspecting a lawn stadium with the vegetation inspection apparatus 11 will now be described with reference to FIGS. 4 to 6.

Figure 4:
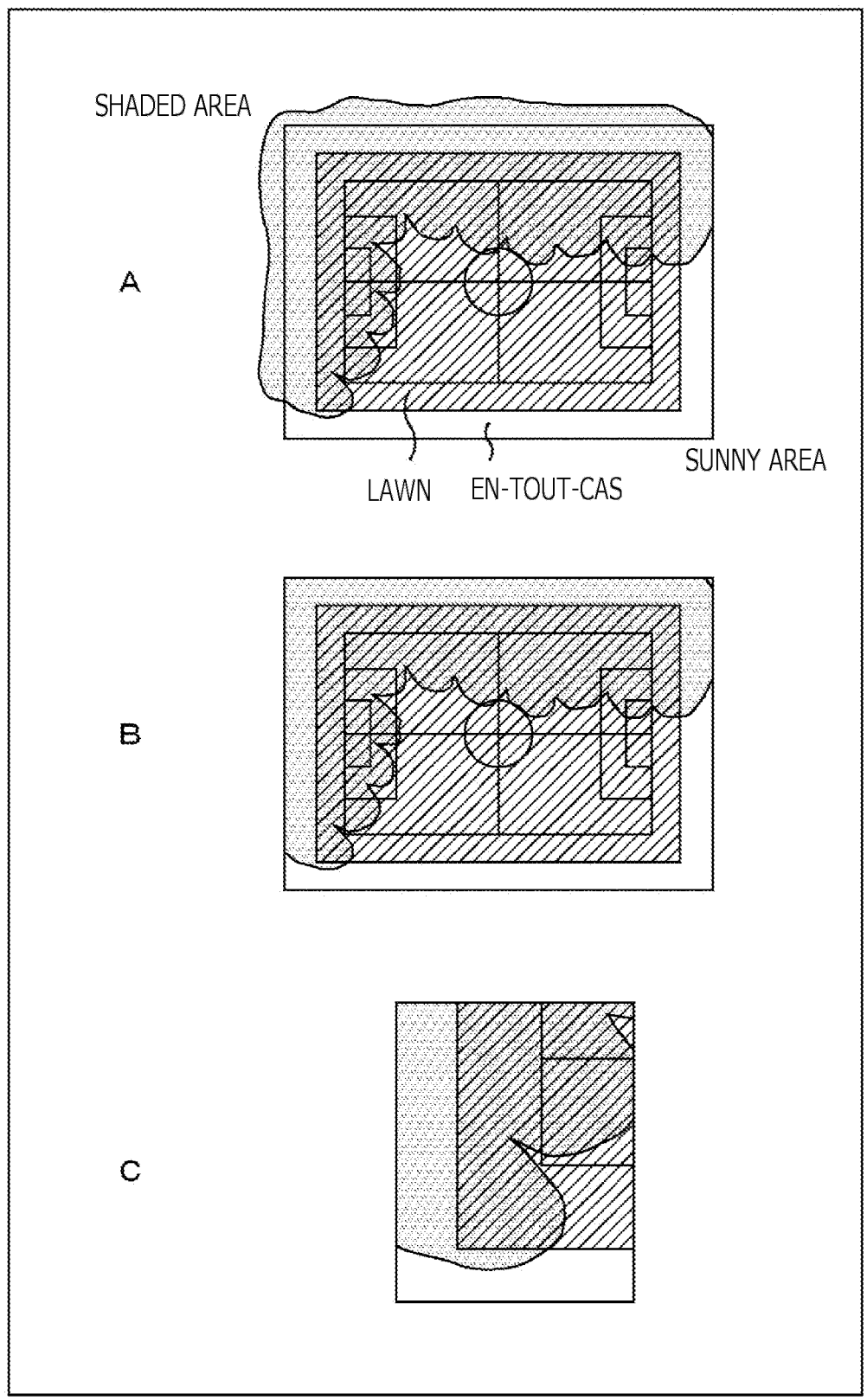
FIG. 4 is a diagram illustrating an example of a lawn stadium.

A lawn stadium is wholly depicted at A in FIG. 4. A field where sport is played is entirely covered with lawn. Additionally, a predetermined width of a portion outside of the field is also covered with lawn. A portion outside the lawn-covered area is covered, for example, with a well-drained, rusty red en-tout-cas pavement. In this case, the reflectance properties of the lawn vary with its vegetation state. However, the reflectance properties of the en-tout-cas pavement remain unchanged. Therefore, when the reflectance properties of the en-tout-cas pavement are measured in advance, the en-tout-cas pavement can be used as the reference reflective plate 13 depicted in FIG. 1.

Further, the vegetation inspection apparatus 11 is, for example, installed at a location that provides a commanding view of the whole lawn stadium (e.g., installed at an uppermost spectator's seat), and is capable of sensing the whole lawn stadium in a wide-angle mode as depicted at C in FIG. 4 and sensing a part of the lawn stadium in a telephoto mode as depicted at C in FIG. 4. Here, in a case where a captured image includes a sunny area and a shaded area, appropriate exposure control needs to be exercised by using pixels detecting red light R and pixels detecting infrared light IR.

Detection signals of reflected red light R, reflected infrared light IR, sunny area, and shaded area of lawn and detection signals of reflected red light R, reflected infrared light IR, sunny area, and shaded area of en-tout-cas will now be described with reference to FIGS. 5 and 6.

Figure 5:
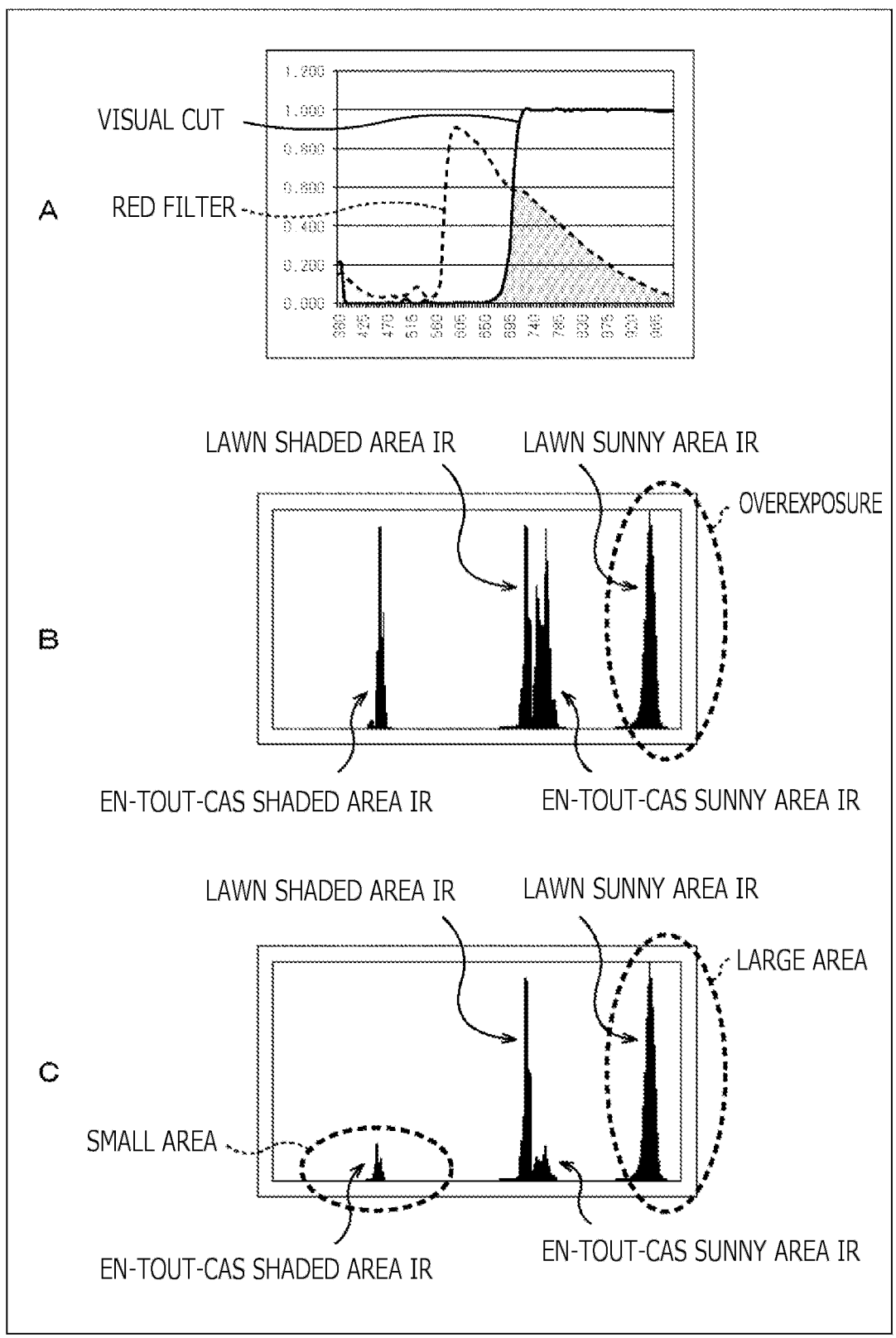
FIG. 5 is a diagram illustrating a detection signal of reflected infrared light IR.

For example, a visual cut filter having properties depicted at A in FIG. 5 is disposed for pixels detecting infrared light IR.

A histogram depicted at B in FIG. 5 depicts a sensing result concerning infrared light IR (e.g., one image frame, that is, an array of n sets of 8-pixel optical filters in FIG. 1) that is obtained when a part of the lawn stadium is sensed as indicated at C in FIG. 4. For example, the horizontal axis at B in FIG. 5 represents the intensity of detection signals of all pixels (e.g., the intensity prevailing when the detection signals are formed of 12 bits while the leftmost end is 0 and the rightmost end is 211), and the vertical axis at B in FIG. 5 represents the frequency of detection signals of pixels detecting infrared light IR among the detection signals of all pixels. When a part of the lawn stadium is sensed in the telephoto mode, the intensity in a sunny area of lawn is likely to be excessively high as indicated at B in FIG. 5 so that a captured image becomes overexposed.

A histogram depicted at C in FIG. 5 is obtained when the lawn stadium depicted at B in FIG. 4 is wholly sensed. The horizontal axis represents intensity, and the vertical axis represents frequency. As indicated at C in FIG. 5, when the whole lawn stadium is sensed in the wide-angle mode, for example, an adequate dynamic range can easily be obtained for the sunny area of lawn, which is subjected to large-area sensing, but an adequate dynamic range cannot easily be obtained for the shaded area of en-tout-cas, which is subjected to small-area sensing.

Figure 6:
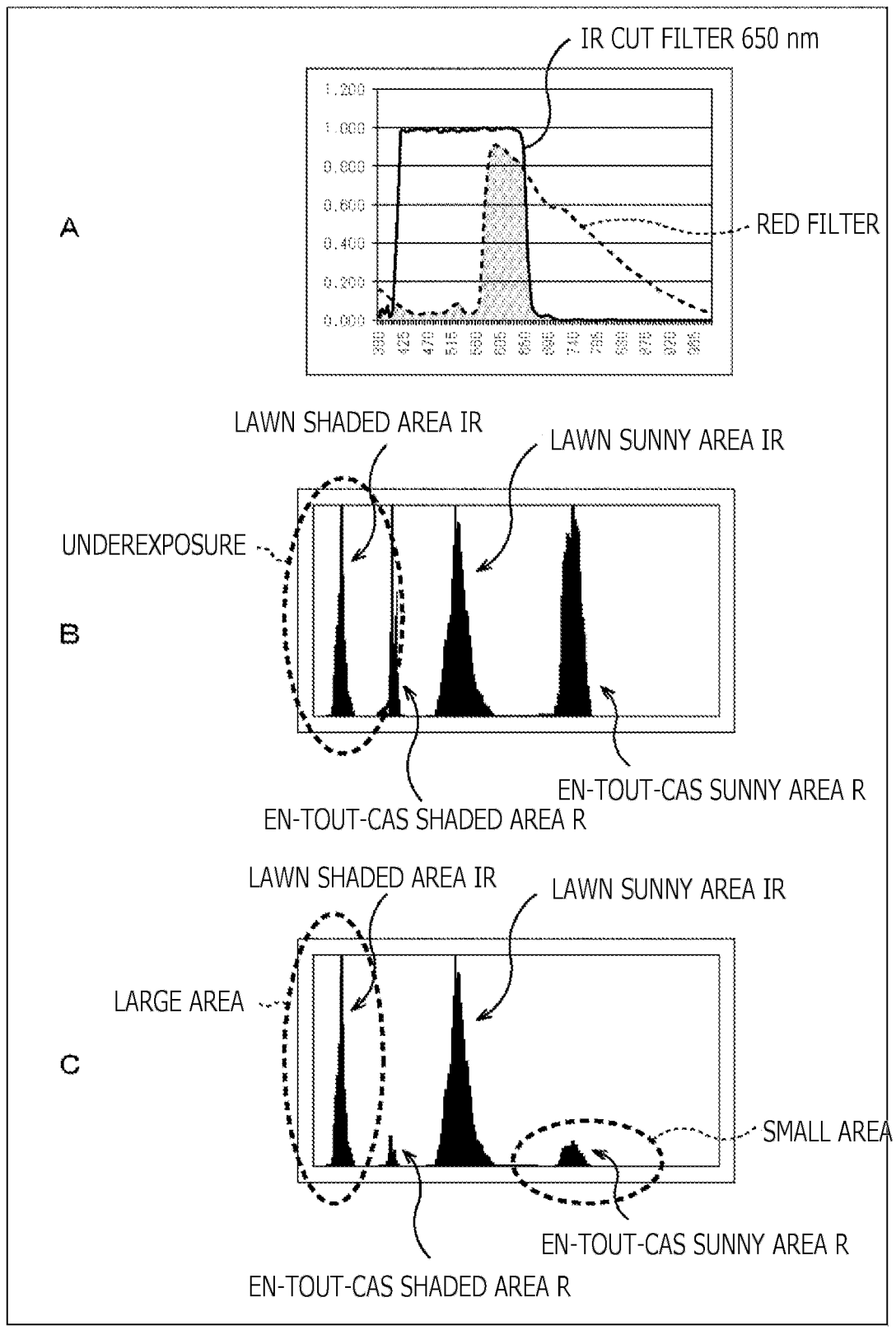
FIG. 6 is a diagram illustrating a detection signal of reflected red light R.

Further, a red filter having the properties depicted at A in FIG. 6 is disposed for pixels detecting red light R.

A histogram depicted at B in FIG. 6 depicts a sensing result concerning red light R that is obtained when a part of the lawn stadium is sensed as indicated at C in FIG. 4. More specifically, the horizontal axis at B in FIG. 6 represents the intensity of detection signals of all pixels, and the vertical axis at B in FIG. 6 represents the frequency of detection signals of pixels detecting red light R among the detection signals of all pixels. When a part of the lawn stadium is sensed in the telephoto mode, the intensity in a shaded area of lawn is likely to be excessively low as indicated at B in FIG. 6 so that a captured image becomes underexposed.

A histogram depicted at C in FIG. 6 is obtained when the lawn stadium depicted at B in FIG. 4 is wholly sensed. The horizontal axis represents intensity, and the vertical axis represents frequency. As indicated at C in FIG. 6, when the whole lawn stadium is sensed in the wide-angle mode, for example, an adequate dynamic range can easily be obtained for the shaded area of lawn, which is subjected to large-area sensing, but an adequate dynamic range cannot easily be obtained for the sunny area of en-tout-cas, which is subjected to small-area sensing.

As implied above, proper exposure was not easily achieved in the past by pixels detecting red light R and pixels detecting infrared light IR under conditions where overexposure or underexposure was likely to occur (wide-angle or telephoto mode, shaded or sunny area). Further, in a case where the whole lawn stadium was sensed in the wide-angle mode, the en-tout-cas was subjected to small-area sensing. Therefore, it was difficult to obtain an adequate dynamic range of light reflected from the en-tout-cas.

In view of the above circumstances, the vegetation inspection apparatus 11 adopts an inspection method that makes it possible to select proper exposure settings for pixels detecting red light R and pixels detecting infrared light IR and perform proper gain calibration for detection signals of red light R and infrared light IR. This enables the vegetation inspection apparatus 11 to calculate a proper normalized difference vegetation index NDVI and inspect vegetation with increased accuracy.

<Method of Inspection by Vegetation Inspection Apparatus>

An example of a method of inspection by the vegetation inspection apparatus 11 depicted in FIG. 1 will now be described with reference to FIGS. 7 to 10.

Figure 7:
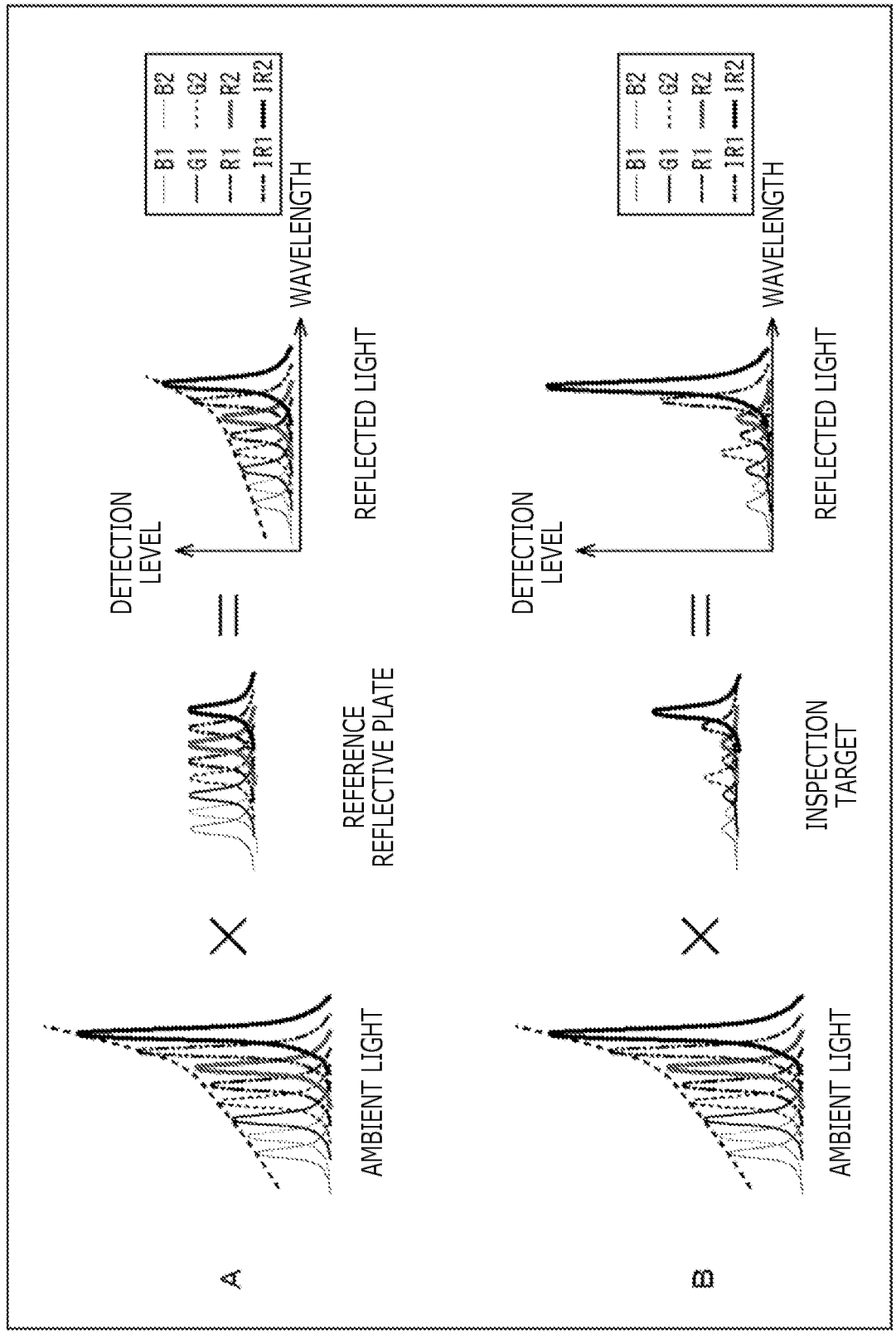
FIG. 7 is a diagram illustrating spectroscopic properties of reflected light.

FIG. 7 is a diagram illustrating the spectroscopic properties of reflected light that is incident on the vegetation inspection apparatus 11 through the optical system 21.

For example, ambient light has such spectroscopic properties that its brightness increases with an increase in its wavelength (i.e., from the first blue light B1 to the second infrared light IR2). The spectroscopic properties of ambient light reflected from the inspection target 12 and the reference reflective plate 13 are determined by multiplying the respective reflectance properties of the ambient light by the spectroscopic properties of the inspection target 12 and of the reference reflective plate 13.

For example, the reference reflective plate 13 having uniform reflectance properties with respect to all wavelengths as indicated at A in FIG. 7 will now be described as an example. Light reflected from the above-mentioned reference reflective plate 13 has spectroscopic properties that are determined by multiplying the spectroscopic properties of ambient light by the reflectance properties of the reference reflective plate 13. Thus, the detection level of the reflected light in the vegetation inspection apparatus 11 increases with an increase in wavelength.

Meanwhile, as indicated at B in FIG. 7, the inspection target 12 has reflectance properties based on the absorption properties described earlier with reference to FIG. 2. Therefore, light reflected from the inspection target 12 has spectroscopic properties that are determined by multiplying the spectroscopic properties of ambient light by the reflectance properties of the inspection target 12. Thus, the detection level of the reflected light in the vegetation inspection apparatus 11 is, for example, low for red light R and high for infrared light IR.

As described above, the light reflected from the inspection target 12 and the light reflected from the reference reflective plate 13 are each incident on the vegetation inspection apparatus 11 so that the inspection target 12 and the reference reflective plate 13 are observed as an image as indicated in the display section 14 depicted in FIG. 1.

A sensitivity adjustment process will now be described with reference to FIGS. 8 and 9.

Figure 8:
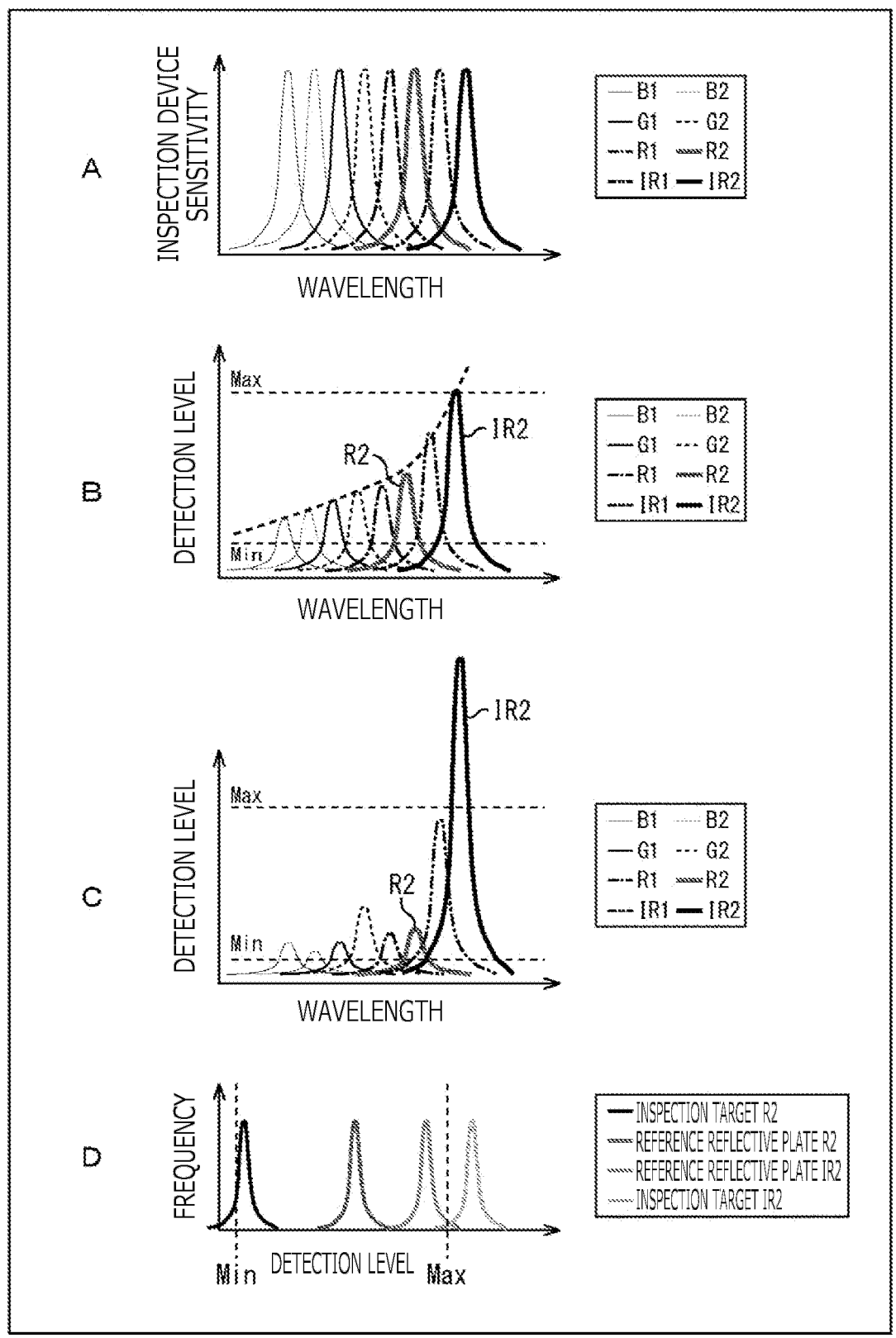
FIG. 8 is a diagram illustrating a sensitivity adjustment process.

An exemplary sensitivity setting of the sensing element 32 in the vegetation inspection apparatus 11 is depicted at A in FIG. 8. For example, a flat sensitivity setting is adopted as an initial state so that light is detected at a uniform sensitivity within all wavelength regions.

Consequently, as indicated at B in FIG. 8, the detection level of light reflected from the reference reflective plate 13 coincides with the detection level of reflected light depicted at A in FIG. 7 in a case where a flat sensitivity setting is adopted by the vegetation inspection apparatus 11. Similarly, as indicated at C in FIG. 8, the detection level of light reflected from the inspection target 12 coincides with the detection level of reflected light depicted at B in FIG. 7 in a case where a flat sensitivity setting is adopted by the vegetation inspection apparatus 11.

Spectral properties depicted at B and C in FIG. 8 are presented in the form of an image indicative of wavelength-specific intensity of light reflected from the reference reflective plate 13 and the inspection target 12, and are not directly observable, for example, at the display section 14 depicted in FIG. 1. In reality, a value integrated for each spectrum is outputted as a detection signal from the sensing element 32, subjected to signal processing in the signal processing block 24, and observed as a waveform-specific image.

The signal processing block 24 then calculates a histogram indicating the detection level of each wavelength region (first blue light B1, second blue light B2, first green light G1, second green light G2, first red light R1, second red light R2, first infrared light IR1, and second infrared light IR2) of light reflected from the reference reflective plate 13 and the inspection target 12.

Depicted at D in FIG. 8 are histograms of the second red light R2 and second infrared light IR2 reflected from the reference reflective plate 13 and histograms of the second red light R2 and second infrared light IR2 reflected from the inspection target 12, which are both among the histograms obtained by performing calculations on all wavelength regions of the reflected light.

At D in FIG. 8, the horizontal axis indicates a detection level, and the vertical axis indicates a histogram (represents frequency). The detection level of the second infrared light IR2 from the inspection target 12 is very high (C in FIG. 8). Therefore, the detection level of a histogram of the second infrared light IR2 from the inspection target 12 is mostly higher than the maximum value Max of a dynamic range detectable by the sensing element 32. Consequently, the second infrared light IR2 from the inspection target 12 is likely to become overexposed.

Further, the detection level of the second red light R2 from the inspection target 12 is low (C in FIG. 8). Therefore, the detection level of a histogram of the second red light R2 from the inspection target 12 is partly lower than the minimum value Min of a dynamic range detectable by the sensing element 32. Consequently, the second red light R2 from the inspection target 12 is likely to become underexposed. As indicated at A in FIG. 8, the reference reflective plate 13 has flat properties over the entire bandwidth so that the spectral intensity of the ambient light is fully acquired.

In order to calculate a proper normalized difference vegetation index NDVI, therefore, it is preferable to avoid a situation where the detection level of the second infrared light IR2 from the inspection target 12 becomes overexposed and a situation where the detection level of the second red light R2 from the inspection target 12 becomes underexposed.

Under the above circumstances, the vegetation inspection apparatus 11 controls the sensitivity of the sensing element 32 on an individual spectroscopic component basis so as to ensure that the detection level of the second red light R2 from the inspection target 12 and the detection level of the second infrared light IR2 from the inspection target 12 are both within the dynamic range.

Figure 9:
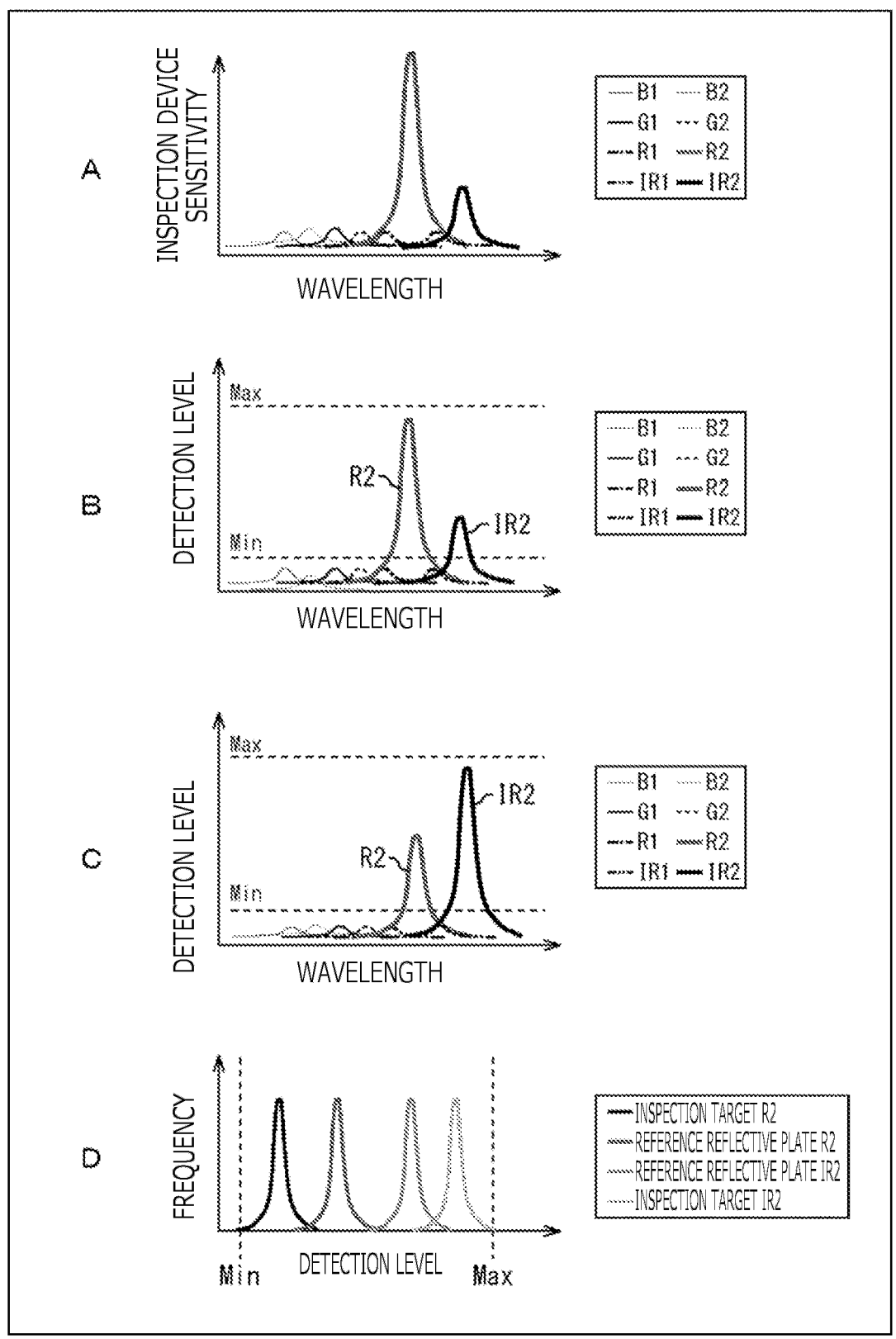
FIG. 9 is a diagram illustrating a sensitivity adjustment process.

Depicted at A in FIG. 9 is an exemplary sensitivity setting for the sensing element 32 controlled by the control block 25. Specifically, as compared to a flat sensitivity setting depicted in at A in FIG. 8, the control block 25 selects a high sensitivity setting for the second red light R2 and a low sensitivity setting for the second infrared light IR2. Further, as spectroscopic components other than the second red light R2 and the second infrared light IR2 are unnecessary for calculating the normalized difference vegetation index NDVI, the control block 25 exercises control so that the sensitivity to such unnecessary spectroscopic components is substantially zero (lower than the minimum value Min of the detection level).

Consequently, as indicated at B in FIG. 9, the detection level of light reflected from the reference reflective plate 13 is determined by multiplying the detection level depicted at B in FIG. 8 by the sensitivity setting for the sensing element 32 that is depicted at A in FIG. 9. Similarly, as indicated at C in FIG. 9, the detection level of light reflected from the inspection target 12 is determined by multiplying the detection level depicted at C in FIG. 8 by the sensitivity setting for the sensing element 32 that is depicted at A in FIG. 9.

Accordingly, as indicated at D in FIG. 9, the detection level of the second red light R2 from the inspection target 12 and the detection level of the second infrared light IR2 from the inspection target 12 are controlled so that they are both within the dynamic range. That is to say, overexposure and underexposure described with reference to D in FIG. 8 are avoided.

Incidentally, the second red light R2 and second infrared light IR2 from the inspection target 12 contain the spectroscopic properties of the ambient light. Therefore, it is necessary to eliminate the spectroscopic properties of the ambient light from the second red light R2 and second infrared light IR2 reflected from the inspection target 12 and obtain the second red light R2 and the second infrared light IR2 that correspond to the reflectance properties of the inspection target 12 (the spectral properties of the reflected light that prevail when the ambient light is flat). Under such circumstances, the vegetation inspection apparatus 11 performs the gain calibration process on detection signals of the second red light R2 and second infrared light IR2 from the inspection target 12 by reference to the second red light R2 and second infrared light IR2 from the reference reflective plate 13.

Figure 10:
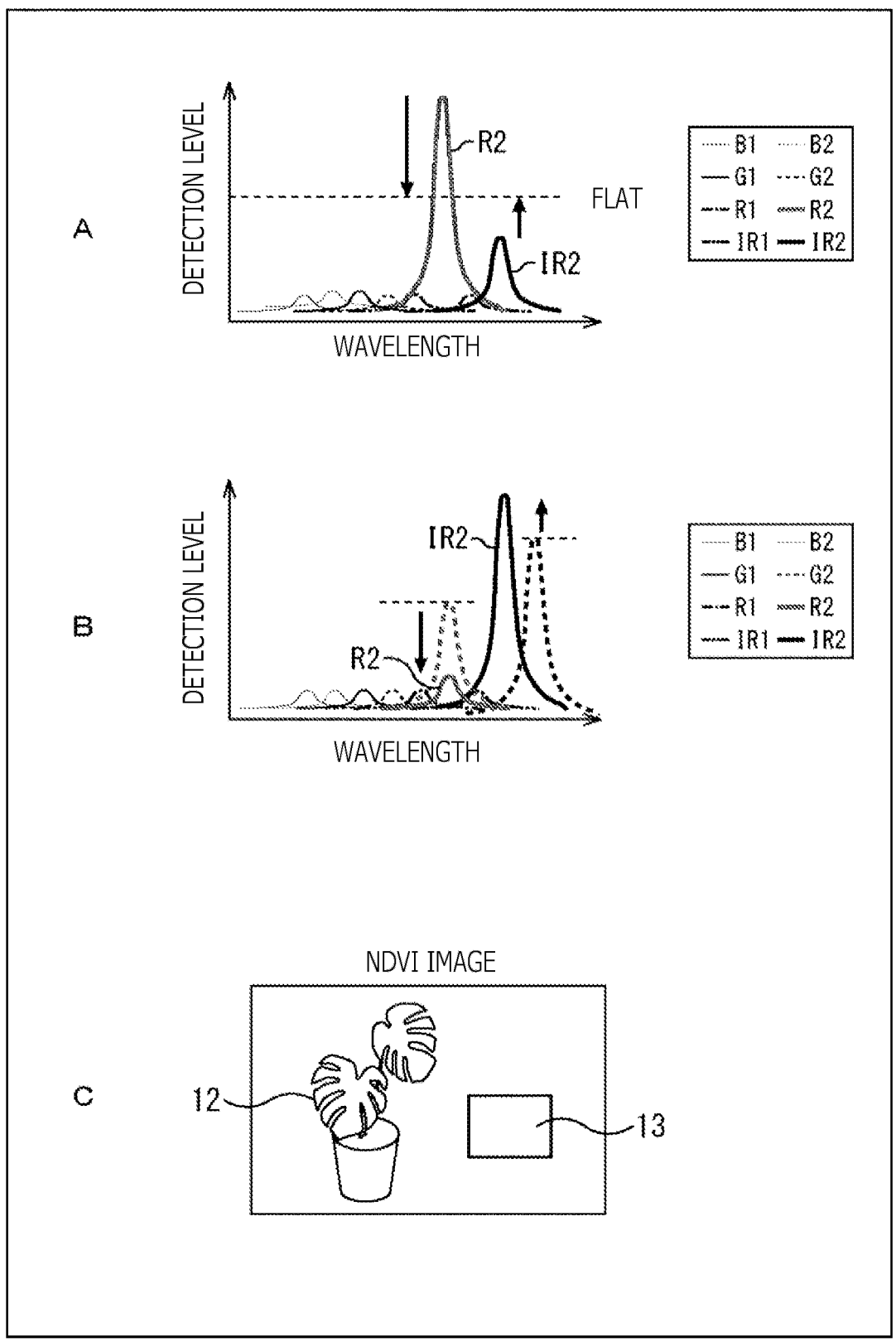
FIG. 10 is a diagram illustrating a gain calibration process.

FIG. 10 is a diagram illustrating the gain calibration process that is performed on the detection signals of the second red light R2 and second infrared light IR2 from the inspection target 12.

First of all, as indicated at A in FIG. 10, calibration gains for providing a flat detection level (uniform detection level) of the second red light R2 and second infrared light IR2 from the reference reflective plate 13 are determined. More specifically, the signal processing block 24 calculates the calibration gain for R and the calibration gain for IR. The calibration gain for R attenuates the second red light R2 from the reference reflective plate 13 to a detection level that flattens the second red light R2. The calibration gain for IR amplifies the second infrared light IR2 from the reference reflective plate 13 to a detection level that flattens the second infrared light IR2.

As indicated in Equation (1) above, the normalized difference vegetation index NDVI is a value based on the ratio of spectral change. Thus, the normalized difference vegetation index NDVI is a value based on the ratio between the second red light R2 and the second infrared light IR. That is to say, the absolute values of the second red light R2 and second infrared light IR2 do not affect the normalized difference vegetation index NDVI. Therefore, any values may be set as the detection levels that flatten the second red light R2 and second infrared light IR2 from the reference reflective plate 13.

Depicted at B in FIG. 10 are the detection levels of the second red light R2 and second infrared light IR2 from the inspection target 12 that are configured on the basis of the calibration gains determined in accordance with the detection levels of the second red light R2 and second infrared light IR2 from the reference reflective plate 13. That is to say, the signal processing block 24 corrects the detection level of the second red light R2 from the inspection target 12 in accordance with the calibration gain for R, which attenuates the second red light R2 from the reference reflective plate 13 to a detection level that flattens the second red light R2. Similarly, the signal processing block 24 corrects the detection level of the second infrared light IR2 from the inspection target 12 in accordance with the calibration gain for IR, which amplifies the second infrared light IR2 from the reference reflective plate 13 to a detection level that flattens the second red light R2.

When the above-described gain calibration process is performed, the spectroscopic properties of the ambient light can be eliminated from the detection levels of the second red light R2 and second infrared light IR2 from the inspection target 12. The signal processing block 24 then uses Equation (1) above to calculate the normalized difference vegetation index NDVI on the basis of the detection signals of the second red light R2 and second infrared light IR2 from the inspection target 12 from which the spectroscopic properties of the ambient light are eliminated. The vegetation inspection apparatus 11 is able to directly output the normalized difference vegetation index NDVI calculated in the above manner.

Further, as indicated at C in FIG. 10, the vegetation inspection apparatus 11 may generate an NDVI image by visualizing the inspection target 12 on the basis of the calculated normalized difference vegetation index NDVI and output the generated NDVI image to the display section 14 depicted in FIG. 1. For example, the vegetation inspection apparatus 11 may generate a grayscale NDVI image based on the value of the normalized difference vegetation index NDVI or generate an NDVI image by mapping the value of the NDVI by using predetermined color components of visible light such as red, blue, and green.

As described with reference to FIGS. 7 to 10, in accordance with the reflectance properties of the inspection target 12 and the state of the ambient light (the light reflected from the reference reflective plate 13), the vegetation inspection apparatus 11 calibrates the gain by controlling the sensitivity to spectroscopic components, which are necessary for calculating the normalized difference vegetation index NDVI. This enables the vegetation inspection apparatus 11 to avoid the overexposure and underexposure of the detection level and generate an NDVI image from which the spectroscopic properties of ambient light are eliminated.

Figure 11:
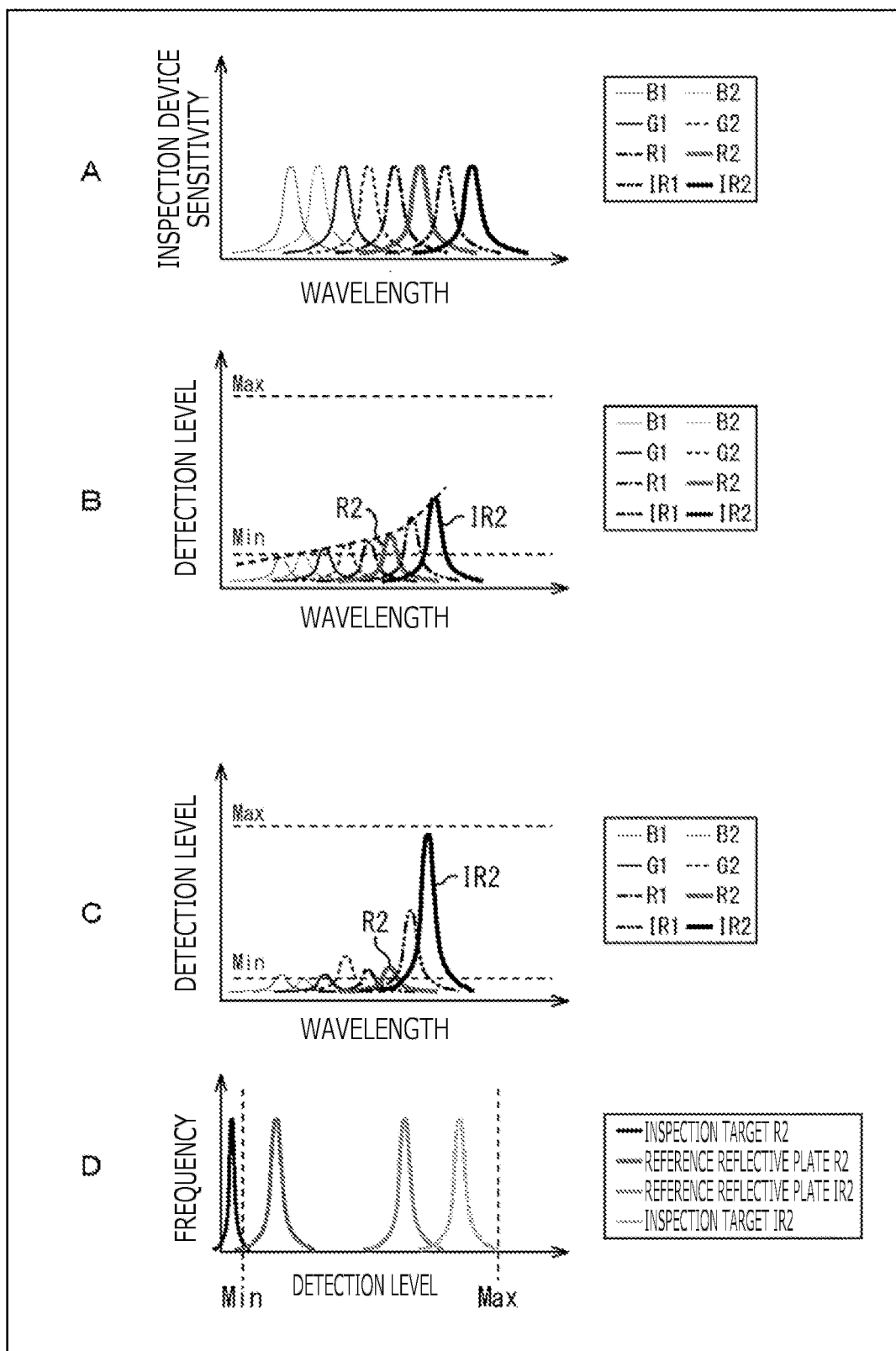
FIG. 11 is a diagram illustrating a sensitivity adjustment process at a flat sensitivity setting.
Figure 12:
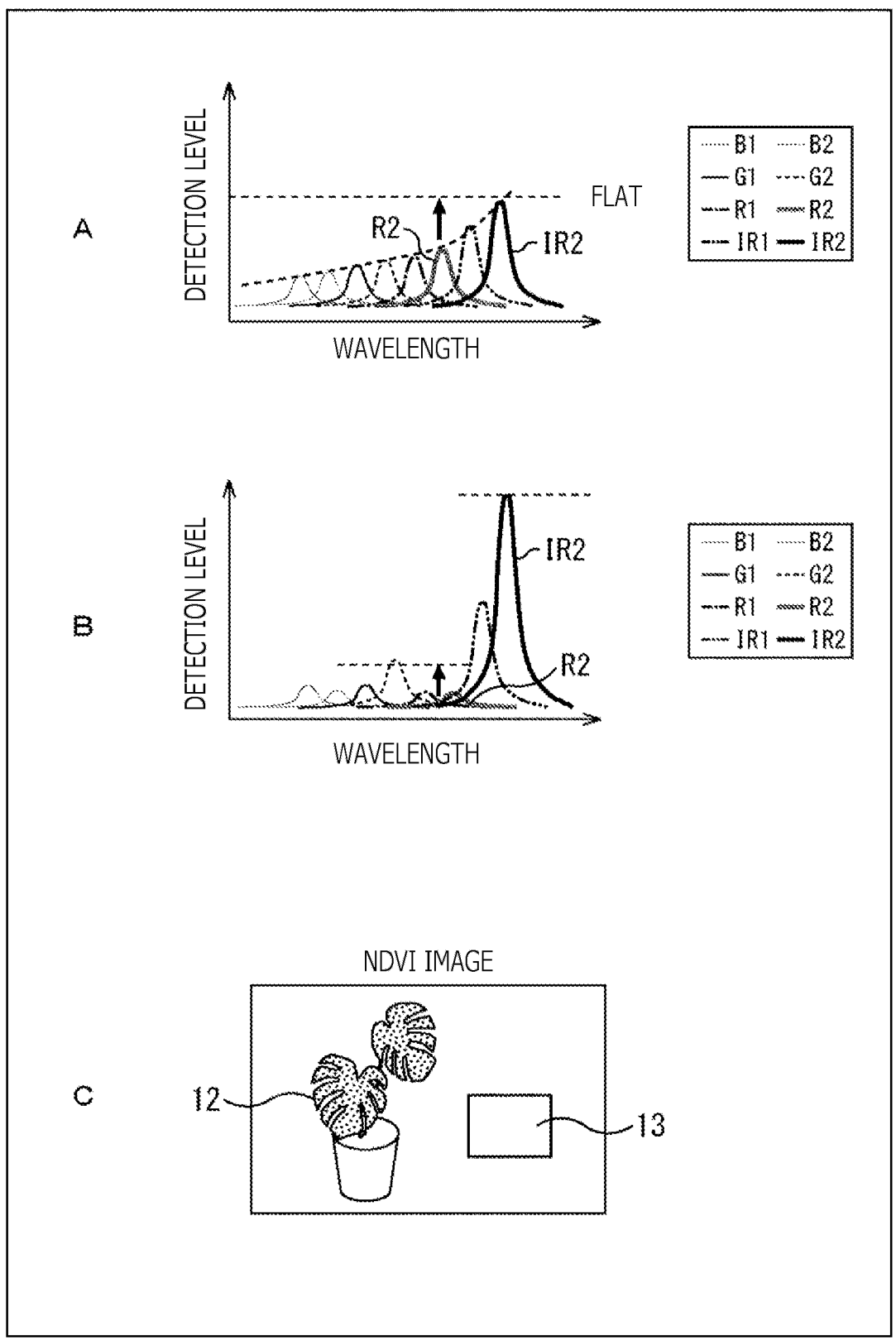
FIG. 12 is a diagram illustrating a gain calibration process at a flat sensitivity setting.

Referring now to FIGS. 11 and 12, effects produced by performing the above-described sensitivity adjustment process and gain calibration process will be described in comparison with the results obtained when a flat sensitivity setting is adopted for the sensing element 32.

An example depicted at A in FIG. 11 represents a case where the sensitivity of the sensing element 32 is lowered to avoid the overexposure of the detection level of the second infrared light IR2 from the inspection target 12 while a flat sensitivity setting is maintained.

Accordingly, as indicated at B in FIG. 11, the detection level of light reflected from the reference reflective plate 13 is determined by multiplying the detection level depicted at B in FIG. 8 by the sensitivity setting for the sensing element 32, which is depicted at A in FIG. 11. Similarly, as indicated at C in FIG. 11, the detection level of light reflected from the inspection target 12 is determined by multiplying the detection level depicted at C in FIG. 8 by the sensitivity setting for the sensing element 32, which is depicted at A in FIG. 11.

In a case where the above-described sensitivity setting is adopted, exposure control is exercised in accordance with the greatest signal. Therefore, as indicated at D in FIG. 11, the detection level of the second infrared light IR2 from the inspection target 12 is controlled to be equal to or lower than the maximum value Max of a dynamic range detectable by the sensing element 32. As a result, however, the detection level of the second red light R2 from the inspection target 12, which is the smallest signal, is mostly lower than the minimum value Min of the dynamic range detectable by the sensing element 32. That is to say, the second red light R2 from the inspection target 12 is likely to become underexposed.

When the above-described gain calibration process is performed in the above-mentioned state, the calibration gain for R for amplifying the second red light R2 from the reference reflective plate 13 is determined so that the detection level of the second red light R2 coincides with the detection level of the second infrared light IR2 from the reference reflective plate 13 as indicated at A in FIG. 12. Even when such a calibration gain for R is used to correct the detection level of the second red light R2 from the inspection target 12, the detection level of the second red light R2 from the inspection target 12 remains low as indicated at B in FIG. 12. That is to say, as the initial detection level of the second red light R2 from the inspection target 12 is excessively low, the detection level cannot be amplified to an adequate level even when the correction is made by using the calibration gain for R. Further, the signal-to-noise ratio (SNR) deteriorates. Consequently, correct results cannot be obtained from an NDVI image (C in FIG. 12) that is generated in the above-described state.

As described above, an appropriate NDVI image cannot be generated in a case where sensitivity is not set for each spectroscopic component. Meanwhile, as described with reference to FIGS. 7 to 10, the vegetation inspection 11 is able to generate a more appropriate NDVI image by setting the sensitivity to each spectroscopic component.

<Process of NDVI Image Generation>

Figure 13:
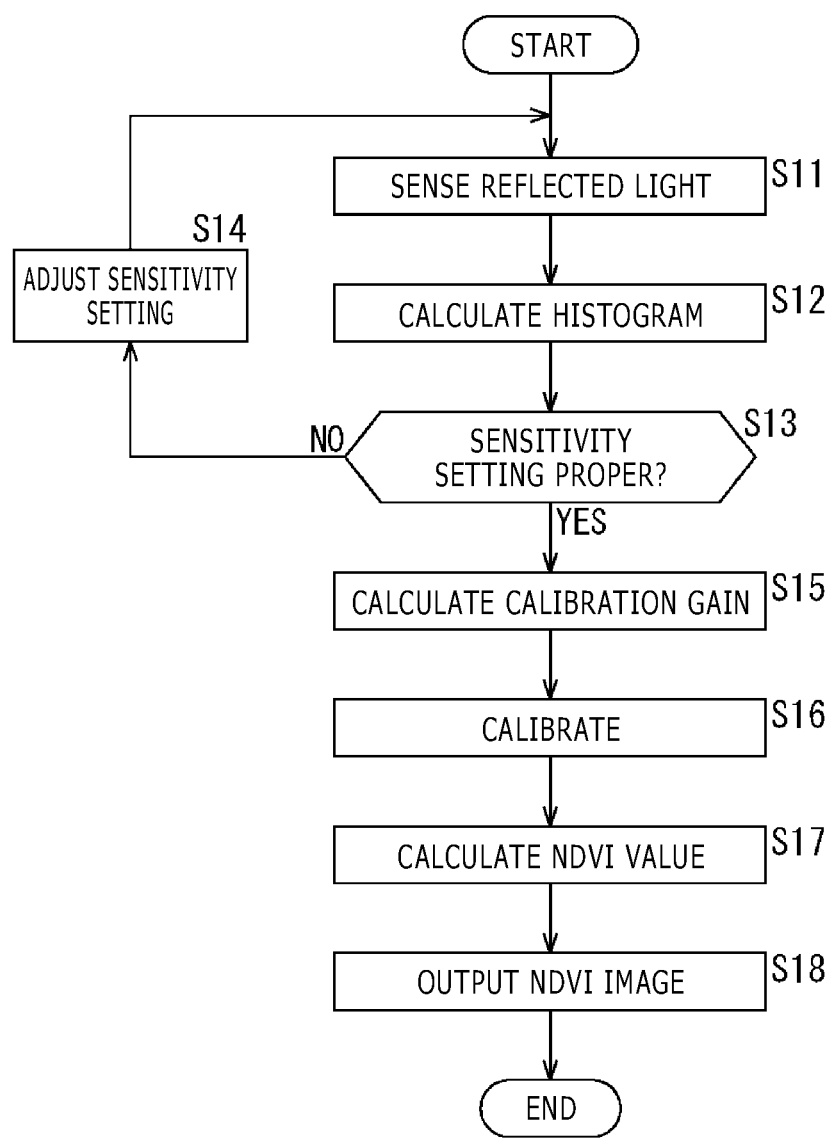
FIG. 13 is a flowchart illustrating a process of generating a normalized difference vegetation index (NDVI) image.

FIG. 13 is a flowchart illustrating a process that is performed by the vegetation inspection apparatus 11 to generate an NDVI image.

The process starts when, for example, an instruction for starting a vegetation inspection is inputted after the vegetation inspection apparatus 11 is installed so as to position the inspection target 12 and the reference reflective plate 13 within a sensing range.

In step S11, the sensing element 32 in the vegetation inspection apparatus 11, for which a flat sensitivity setting is initially adopted as indicated at A in FIG. 8, senses light reflected from the inspection target 12 and the reference reflective plate 13. The sensing element 32 then supplies to the signal processing block 24 a detection signal indicating the detection level of each spectroscopic component, which is depicted, for instance, at B and C in FIG. 8.

In step S12, on the basis of the detection signal supplied from the sensing element 32, the signal processing block 24 calculates a histogram indicating the detection level in every wavelength region of light reflected from the inspection target 12.

In step S13, on the basis of the histogram calculated in step S12, the signal processing block 24 determines, as described with reference to D in FIG. 8, whether or not the sensitivity setting for the sensing element 32 is appropriate. In a case where, for example, the histogram of the second red light R2 from the inspection target 12 is lower than the minimum value Min of a dynamic range detectable by the sensing element 32, the control block 25 determines that the sensitivity setting for the sensing element 32 is inappropriate. Similarly, in a case where the histogram of the second infrared light IR2 from the inspection target 12 is higher than the maximum value Max of the dynamic range detectable by the sensing element 32, the control block 25 determines that the sensitivity setting for the sensing element 32 is inappropriate.

In a case where, in step S13, the signal processing block 24 determines that the sensitivity setting for the sensing element 32 is inappropriate, processing proceeds to step S14. In step S14, the signal processing block 24 determines the sensitivity setting for the sensing element 32 in such a manner that the detection levels of the second red light R2 and second infrared light IR2 from the inspection target 12 are both within the dynamic range, as depicted at D in FIG. 9. The signal processing block 24 then calculates the exposure time for pixels of the sensing element 32 in accordance with the sensitivity setting, and notifies the control block 25 of the calculated exposure time.

Accordingly, the control block 25 controls the exposure time for the pixels of the sensing element 32 to adjust the sensitivity setting for the sensing element 32. For example, the sensitivity setting for the sensing element 32 is adjusted to raise the sensitivity by increasing the exposure time for pixels receiving the second red light R2 within a range where the inspection target 12 is sensed or adjusted to lower the sensitivity by decreasing the exposure time for pixels receiving the second infrared light IR2 within the range where the inspection target 12 is sensed.

Upon completion of step S14, processing returns to step S11. In step S11, the sensing element 32 senses the reflected light in accordance with the sensitivity setting adjusted in step S14. Processing is then repeated until the signal processing block 24 determines in step S13 that the sensitivity setting for the sensing element 32 is appropriate.

Meanwhile, in a case where the signal processing block 24 determines in step S13 that the sensitivity setting for the sensing element 32 is appropriate, processing proceeds to step S15.

In step S15, the signal processing block 24 calculates a calibration gain that flattens the detection levels of the second red light R2 and second infrared light IR2 from the reference reflective plate 13, as described earlier with reference to A in FIG. 10.

In step S16, the signal processing block 24 performs calibration in accordance with the calibration gain calculated in step S15 to eliminate the spectroscopic properties of the ambient light by correcting the detection levels of the second red light R2 and second infrared light IR2 from the inspection target 12.

In step S17, the signal processing block 24 calculates the normalized difference vegetation index NDVI on the basis of detection signals of the second red light R2 and second infrared light IR2 from the inspection target 12, which are calibrated in step S16.

In step S18, based on the normalized difference vegetation index NDVI calculated in step S17, the signal processing block 24 generates an NDVI image depicting the inspection target 12, and outputs the generated NDVI image to the display section 14. The process terminates upon completion of step S18.

As described above, the vegetation inspection apparatus 11 is able to generate an appropriate NDVI image by setting the sensitivity to each of the second red light R2 and second infrared light IR2 from the inspection target 12 and then calibrating their respective detection levels.

Exemplary Configuration of Sensing Element and Control Block

Figure 14:
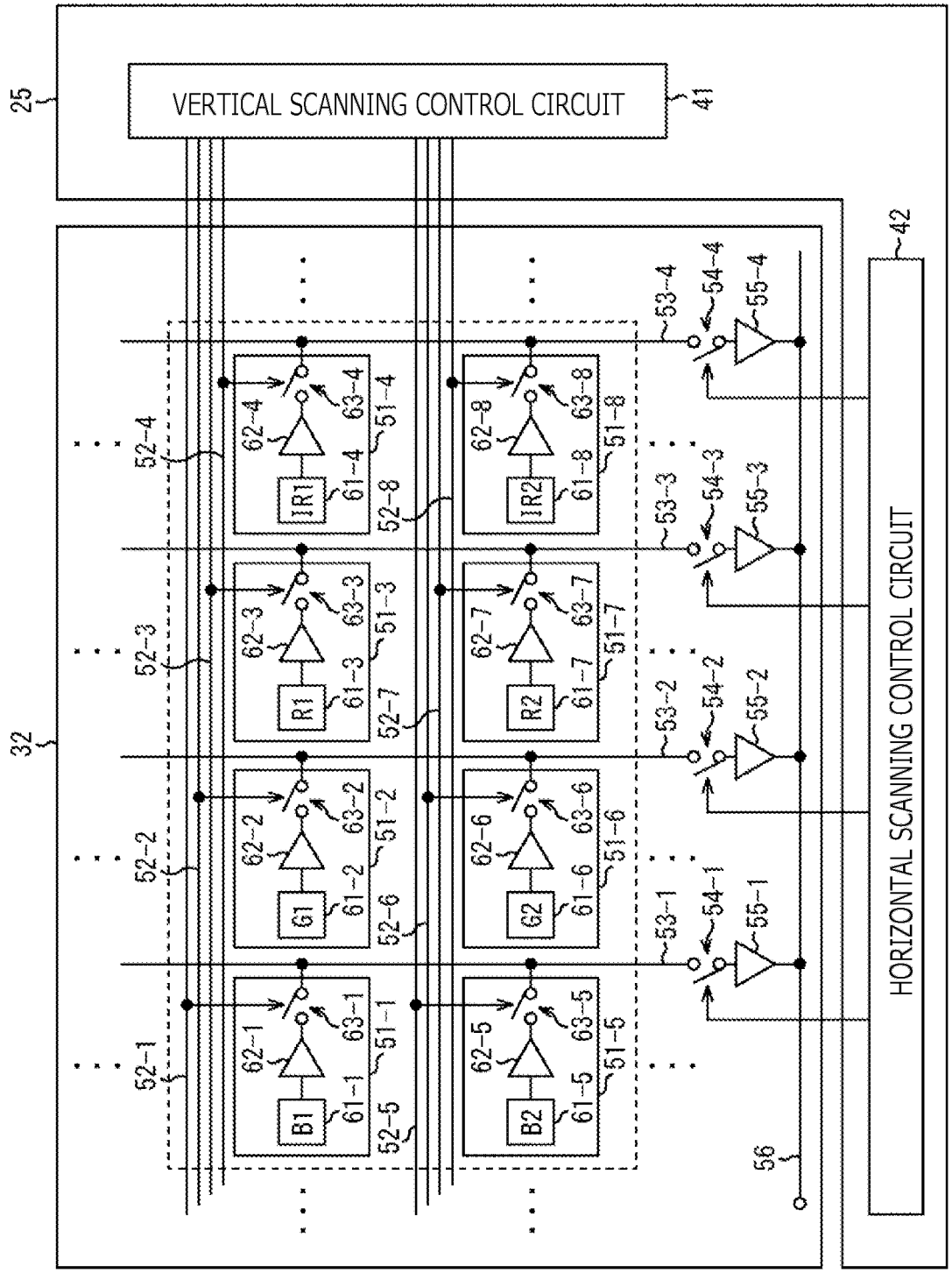
FIG. 14 is a block diagram illustrating an exemplary configuration of a sensing element and a control block.

FIG. 14 is a block diagram illustrating an exemplary configuration of the sensing element 32 and the control block 25.

The control block 25 includes a vertical scanning control circuit 41 and a horizontal scanning control circuit 42. The vertical scanning control circuit 41 controls the vertical scan of the sensing element 32. The horizontal scanning control circuit 42 controls the horizontal scan of the sensing element 32.

The sensing element 32 is formed of a plurality of pixels 51 arranged in a matrix form. The pixels 51 arranged in the horizontal direction are connected to the vertical scanning control circuit 41 through horizontal signal lines 52 in respective rows. Further, the pixels 51 arranged in the vertical direction are connected to vertical signal lines 53 in respective columns. The vertical signal lines 53 are connected to input ends of analog-to-digital converters (ADCs) 55 through switches 54, which are opened and closed under the control of the horizontal scanning control circuit 42. Output ends of the ADCs 55 are connected to an output signal line 56.

The pixels 51 each include a photoelectric conversion section 61, an amplifier section 62, and a switch 63. Light received by the photoelectric conversion section 61 is converted to an electrical charge, amplified by the amplifier section 62, and converted to a signal based on the amount of electrical charge. The switch 63 connects the amplifier section 62 to the vertical signal line 53, and is driven in accordance with a control signal that is supplied from the vertical scanning control circuit 41 through the horizontal signal line 52.

As described above, the sensing element 32 is capable of acquiring from the pixels 51, on an individual vertical signal line 53 basis, signals based on an electrical charge generated by the photoelectric conversion section 61. The horizontal signal lines 52 supplying an exposure time control signal are separated for individual spectroscopic components received by the respective pixels 51. Consequently, exposure time control can be exercised for each spectroscopic component on the basis of one pixel 51 or a predetermined number of pixels 51.

Meanwhile, as illustrated in FIG. 1, the spectroscope 31 is configured so that, by assuming eight different optical filters as one set, n sets of the optical filters are disposed on the whole detection plane of the sensing element 32.

Consequently, eight pixels 51-1 to 51-8 depicted in FIG. 14 form one set. The pixel 51-1 receives the first blue light B1, the pixel 51-2 receives the first green light G1, the pixel 51-3 receivers the first red light R1, and the pixel 51-4 receives the first infrared light IR1. Additionally, the pixel 51-5 receives the second blue light B2, the pixel 51-6 receives the second green light G2, the pixel 51-7 receives the second red light R2, and the pixel 51-8 receives the second infrared light IR2.

The pixel 51-1 is connected to the horizontal signal line 52-1, the pixel 51-2 is connected to the horizontal signal line 52-2, and the pixel 51-3 is connected to the horizontal signal line 52-3. Similarly, the pixels 51-4 to 51-8 are respectively connected to the horizontal signal lines 52-4 to 52-8. Further, although not depicted, pixels 51 receiving light in each same wavelength region are connected to common horizontal signal lines 52.

As described above, the pixels 51-1 to 51-8 are respectively connected to the vertical scanning control circuit 41 through the independent horizontal signal lines 52-1 to 52-8 and capable of controlling the exposure time for each spectroscopic component.

Figure 15:
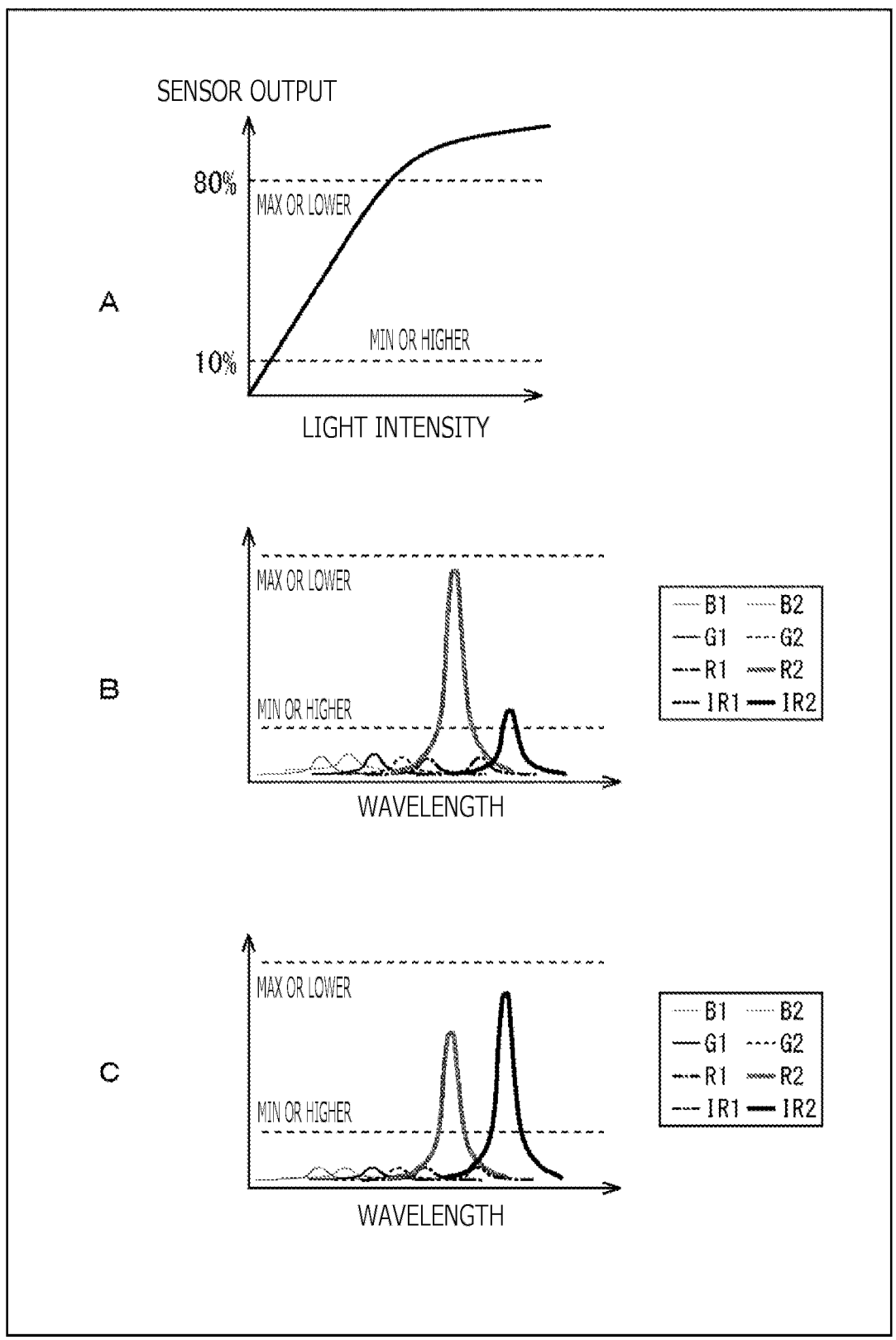
FIG. 15 is a diagram illustrating the dynamic range control of the sensing element.

Referring now to FIG. 15, dynamic range control of the sensing element 32 will be described.

Depicted at A in FIG. 15 is a general relationship between the intensity of light received by the sensing element 32 and a sensor output. Depicted at B in FIG. 15 are spectroscopic properties of light reflected from the reference reflective plate 13. Depicted at C in FIG. 15 are spectroscopic properties of light reflected from the inspection target 12.

As indicated at A in FIG. 15, the linearity of the sensing element 32 deteriorates when the sensor output exceeds 80% of the upper sensitivity limit. Meanwhile, the signal-to-noise ratio (SNR) of the sensing element 32 deteriorates due, for instance, to a dark current when the sensor output lowers.

Accordingly, as indicated at B and C in FIG. 15, the vegetation inspection apparatus 11 controls the exposure time for the second red light R2 and the second infrared light IR2 in such a manner that the dynamic range of the sensing element 32 is lower than 80% and higher than 10% of the upper detection level limit. When the dynamic range is controlled in the above-described manner, the sensing element 32 is able to obtain good sensing results in terms of accuracy and signal-to-noise ratio (SNR).

Alternative Exemplary Method of Inspection by Vegetation Inspection Apparatus

Figure 16:
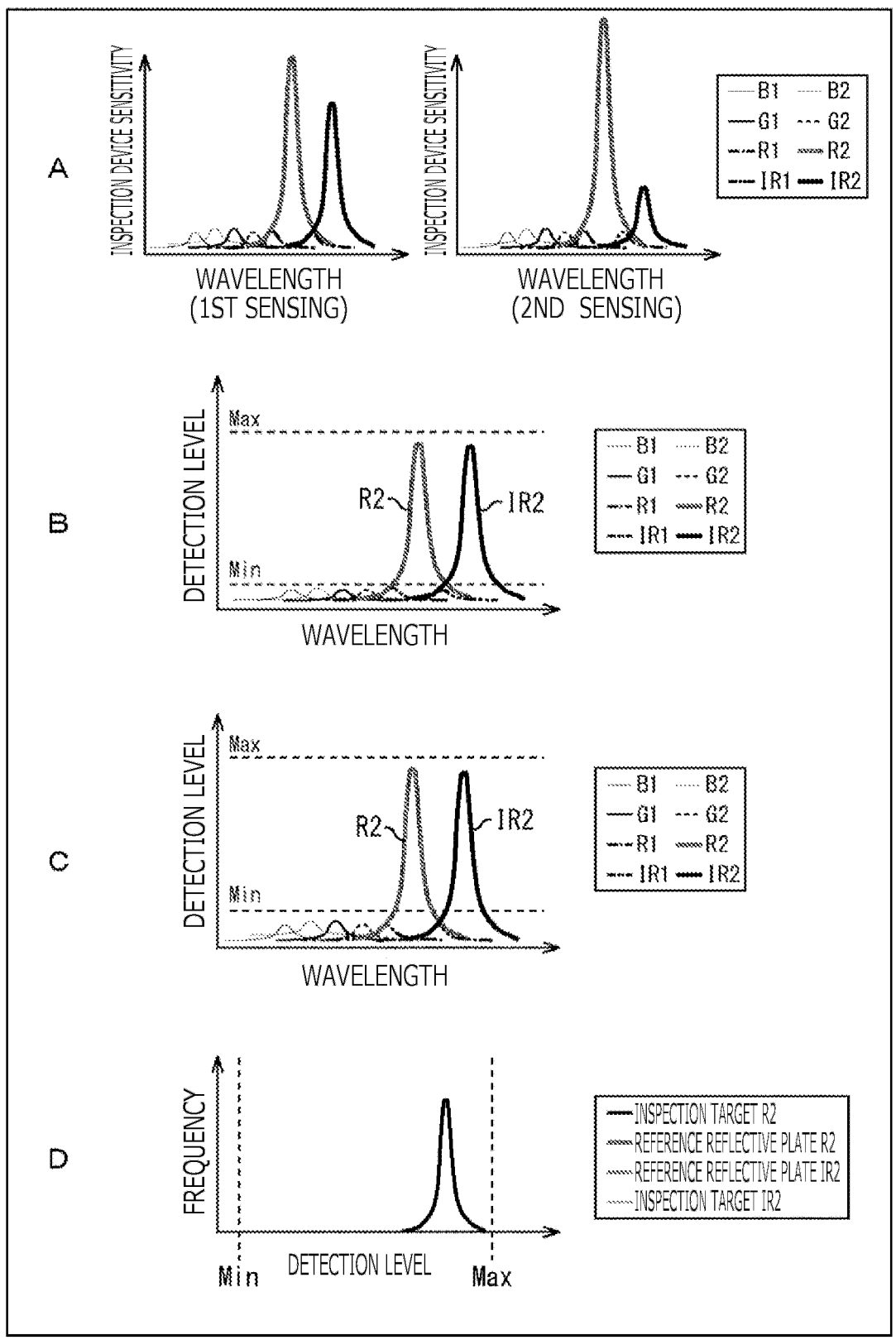
FIG. 16 is a diagram illustrating another example of an inspection method.
Figure 17:
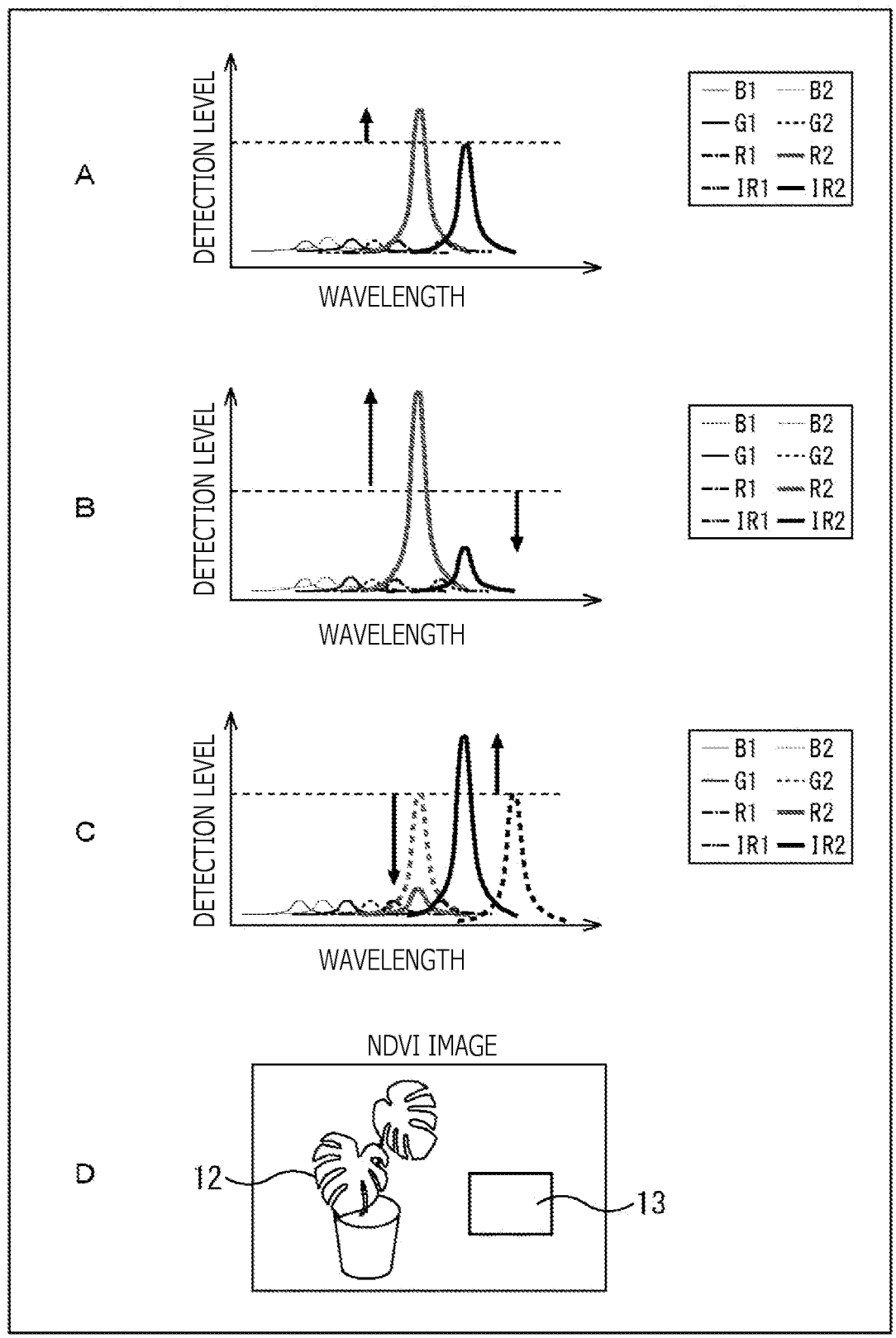
FIG. 17 is a diagram illustrating another example of the inspection method.

Referring now to FIGS. 16 and 17, an alternative exemplary method of inspection by the vegetation inspection apparatus 11 illustrated in FIG. 1 will be described.

The inspection method described earlier with reference to FIGS. 7 to 10 simultaneously senses the inspection target 12 and the reference reflective plate 13. However, improved sensing accuracy can be achieved by separately sensing the inspection target 12 and the reference reflective plate 13.

That is to say, the sensitivity for the first sensing operation, for example, is set so that the intensities of the second red light R2 and second infrared light IR2 from the inspection target 12 are detected under the best conditions as indicated at A in FIG. 16. Similarly, the sensitivity for the second sensing operation is set so that the intensities of the second red light R2 and second infrared light IR2 from the reference reflective plate 13 are detected under the best conditions.

Consequently, the detection levels of the second red light R2 and second infrared light IR2 from the inspection target 12 are both close to and lower than the upper limit of the dynamic range as indicated at B in FIG. 16. Similarly, the detection levels of the second red light R2 and second infrared light IR2 from the reference reflective plate 13 are both close to and lower than the upper limit of the dynamic range as indicated at C in FIG. 16.

Accordingly, as indicated at D in FIG. 16, a histogram indicating the detection level of the second red light R2 and second infrared light IR2 from the inspection target 12 and a histogram indicating the detection level of the second red light R2 and second infrared light IR2 from the reference reflective plate 13 are each observed in an overlapping manner in the vicinity of the upper limit of the dynamic range.

Here, let us assume that the second red light R2 and second infrared light IR2 from the inspection target 12 and the second red light R2 and second infrared light IR2 from the reference reflective plate 13 are detected at the same level as indicated at B and C in FIG. 16. In this instance, the second red light R2 and second infrared light IR2 from the inspection target 12 can be calibrated on the basis of the ratio between a sensitivity adjustment level G1 for the reference reflective plate 13 and a sensitivity adjustment level G2 for the inspection target 12.

More specifically, as indicated at A in FIG. 17, the gain for amplifying the second infrared light IR2 from the reference reflective plate 13 to the same level as the second red light R2 is referred to as the sensitivity adjustment level G1. Further, as indicated at B in FIG. 17, the gain for reducing the second red light R2 from the inspection target 12 and amplifying the second infrared light IR2 from the inspection target 12 to the same level is referred to as the sensitivity adjustment level G2.

Consequently, when the above-described gain calibration process is performed, the sensitivity adjustment level ratio G1/G2 can be used in this instance to reduce the second red light R2 from the inspection target 12 and amplify the second infrared light IR2 from the inspection target 12 as indicated at C in FIG. 17. Accordingly, the detection levels of the second red light R2 and second infrared light IR2 from the inspection target 12 can be determined with high accuracy when the spectroscopic properties of the ambient light are flat. This makes it possible to calculate a more accurate NDVI image (D in FIG. 17).

<Modifications of Spectral Sensor>

Figure 18:
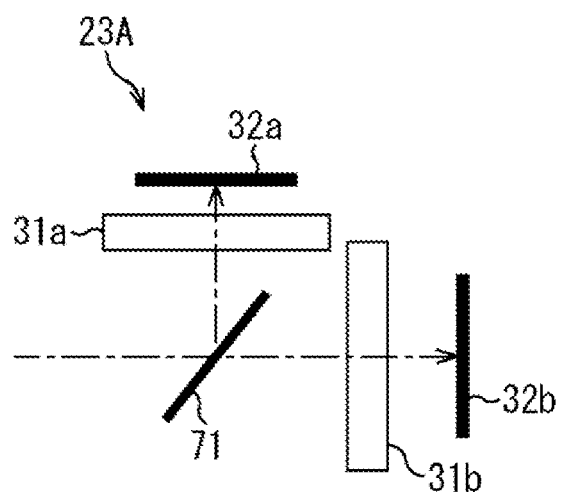
FIG. 18 is a diagram illustrating a first modification of a spectral sensor.

FIG. 18 is a diagram illustrating a first modification of the spectral sensor 23.

As illustrated in FIG. 18, a spectral sensor 23A includes two specific wavelength spectroscopes 31a and 31b, two sensing elements 32a and 32b, and a beam splitter 71.

The beam splitter 71 equally splits a beam of light incident on the spectral sensor 23A into two light beams. One light beam is directed toward the specific wavelength spectroscope 31a and the sensing element 32a, whereas the other light beam is directed toward the specific wavelength spectroscope 31b and the sensing element 32b. A combination of the specific wavelength spectroscope 31a and the sensing element 32a, and a combination of the specific wavelength spectroscope 31b and the sensing element 32b are each disposed in two different directions in which the light beams split by the beam splitter 71 are directed.

The specific wavelength spectroscope 31a is an optical filter that transmits, for example, only the second red light R2 and is disposed in the input stage of the sensing element 32a. Further, the specific wavelength spectroscope 31b is an optical filter that transmits, for example, only the second infrared light IR2 and is disposed in the input stage of the sensing element 32b.

Consequently, the sensing element 32a detects only the second red light R2 dispersed by the specific wavelength spectroscope 31a, and the sensing element 32b detects only the second infrared light IR2 dispersed by the specific wavelength spectroscope 31b.

Subsequently, as is the case with the sensitivity setup process described earlier with reference to FIGS. 8 and 9, the control block 25 depicted in FIG. 1 sets the sensitivity of the sensing element 32a in accordance with the detection level of the second red light R2 from the inspection target 12, and sets the sensitivity of the sensing element 32b in accordance with the detection level of the second infrared light IR2 from the inspection target 12. This ensures that the detection level of the second red light R2 from the inspection target 12 and the detection level of the second infrared light IR2 from the inspection target 12 are both within the dynamic range.

Figure 19:
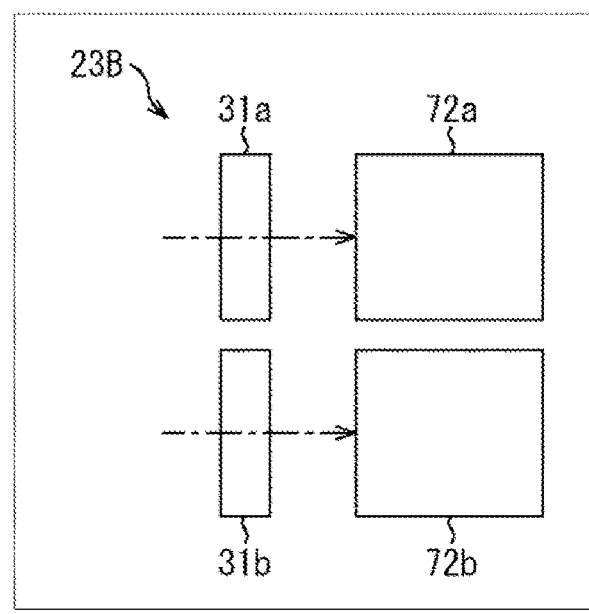
FIG. 19 is a diagram illustrating a second modification of the spectral sensor.

FIG. 19 is a diagram illustrating a second modification of the spectral sensor 23.

As illustrated in FIG. 19, a spectral sensor 23b includes two specific wavelength spectroscopes 31a and 31b and two sensing apparatuses 72a and 72b. The sensing apparatuses 72a and 72b are disposed so that their optical axes are parallel to each other.

The specific wavelength spectroscope 31a is an optical filter that transmits, for example, only the second red light R2 and is disposed in the input stage of the sensing apparatus 72a. Further, the specific wavelength spectroscope 31b is an optical filter that transmits, for example, only the second infrared light IR2 and is disposed in the input stage of the sensing apparatus 72b.

The sensing apparatuses 72a and 72b each include, for example, an optical system, a diaphragm, and a sensing element. In a case where the spectral sensor 23b is employed, the vegetation inspection apparatus 11 does not include the optical system 21 and the diaphragm 22, which are depicted in FIG. 1. The sensing apparatus 72a detects only the second red light R2 dispersed by the specific wavelength spectroscope 31a, and the sensing apparatus 72b detects only the second infrared light IR2 dispersed by the specific wavelength spectroscope 31b.

Subsequently, as is the case with the sensitivity setup process described earlier with reference to FIGS. 8 and 9, the control block 25 depicted in FIG. 1 sets the sensitivity of the sensing element of the sensing apparatus 72a in accordance with the detection level of the second red light R2 from the inspection target 12, and sets the sensitivity of the sensing element of the sensing apparatus 72b in accordance with the detection level of the second infrared light IR2 from the inspection target 12. This ensures that the detection level of the second red light R2 from the inspection target 12 and the detection level of the second infrared light IR2 from the inspection target 12 are both within the dynamic range.

As described with reference to FIGS. 18 and 19, the vegetation inspection apparatus 11 uses a sensing element 32 or a sensing apparatus 72 for each spectroscopic component to be detected, and sets individually the sensitivity of the sensing element 32 or the sensing apparatus 72. This makes it possible to obtain highly accurate inspection results.

<Alternative Method of Detecting Spectroscopic Components>

Figure 20:
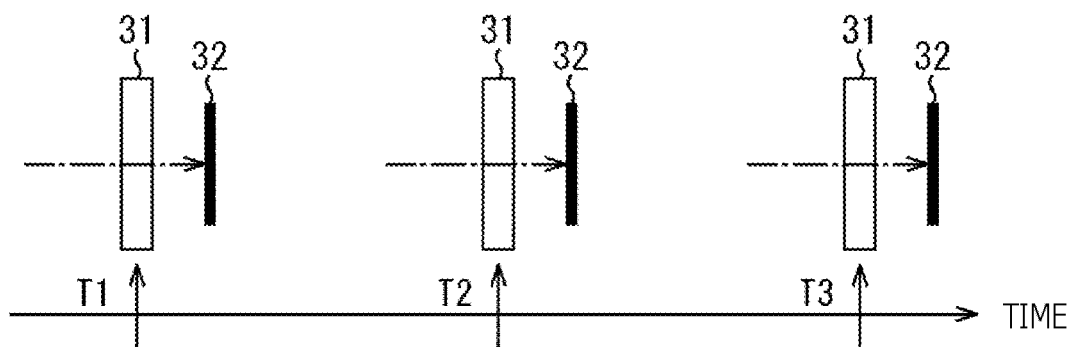
FIG. 20 is a diagram illustrating an example of switching from one spectroscopic component to another in chronological order.
Figure 21:
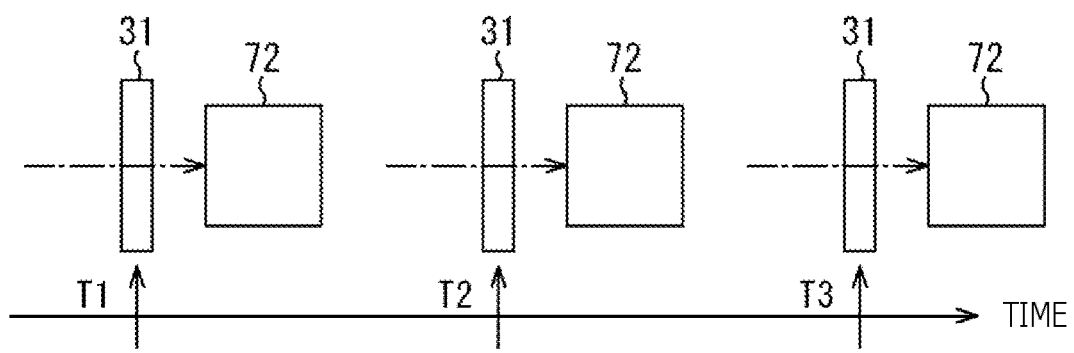
FIG. 21 is a diagram illustrating an example of switching from one spectroscopic component to another in chronological order.

Referring now to FIGS. 20 and 21, an alternative method of detecting a plurality of spectroscopic components will be described.

The above-described vegetation inspection apparatus 11 simultaneously detects a plurality of spectroscopic components dispersed by the spectroscope 31. However, for example, the vegetation inspection apparatus 11 is capable of detecting individual spectroscopic components in an optimal manner by chronologically changing the wavelength to be dispersed by the spectroscope 31. For example, the spectroscope 31 may have a structure for switching from one optical filter to another.

As illustrated, for example, in FIG. 20, the spectroscope 31 can be disposed in the input stage of the sensing element 32 to switch and disperse spectroscopic components at time t1, at time t2, and at time t3. Thus, the detection level of each spectroscopic component can be maintained within the dynamic range by setting the sensitivity of the sensing element 32 in such a manner as to provide an optimal exposure time for a spectroscopic component at each point of time and making a number of detections after each spectroscopic component change by the spectroscope 31.

Similarly, as illustrated in FIG. 21, the spectroscope 31 can be disposed in the input stage of the sensing apparatus 72 to switch and disperse spectroscopic components after another at time t1, at time t2, and at time t3. Thus, the detection level of each spectroscopic component can be maintained within the dynamic range by setting the sensitivity of the sensing apparatus 72 in such a manner as to provide an optimal exposure time for a spectroscopic component at each point of time and making a number of detections after each spectroscopic component change by the spectroscope 31.

Second Embodiment of Vegetation Inspection Apparatus

Figure 22:
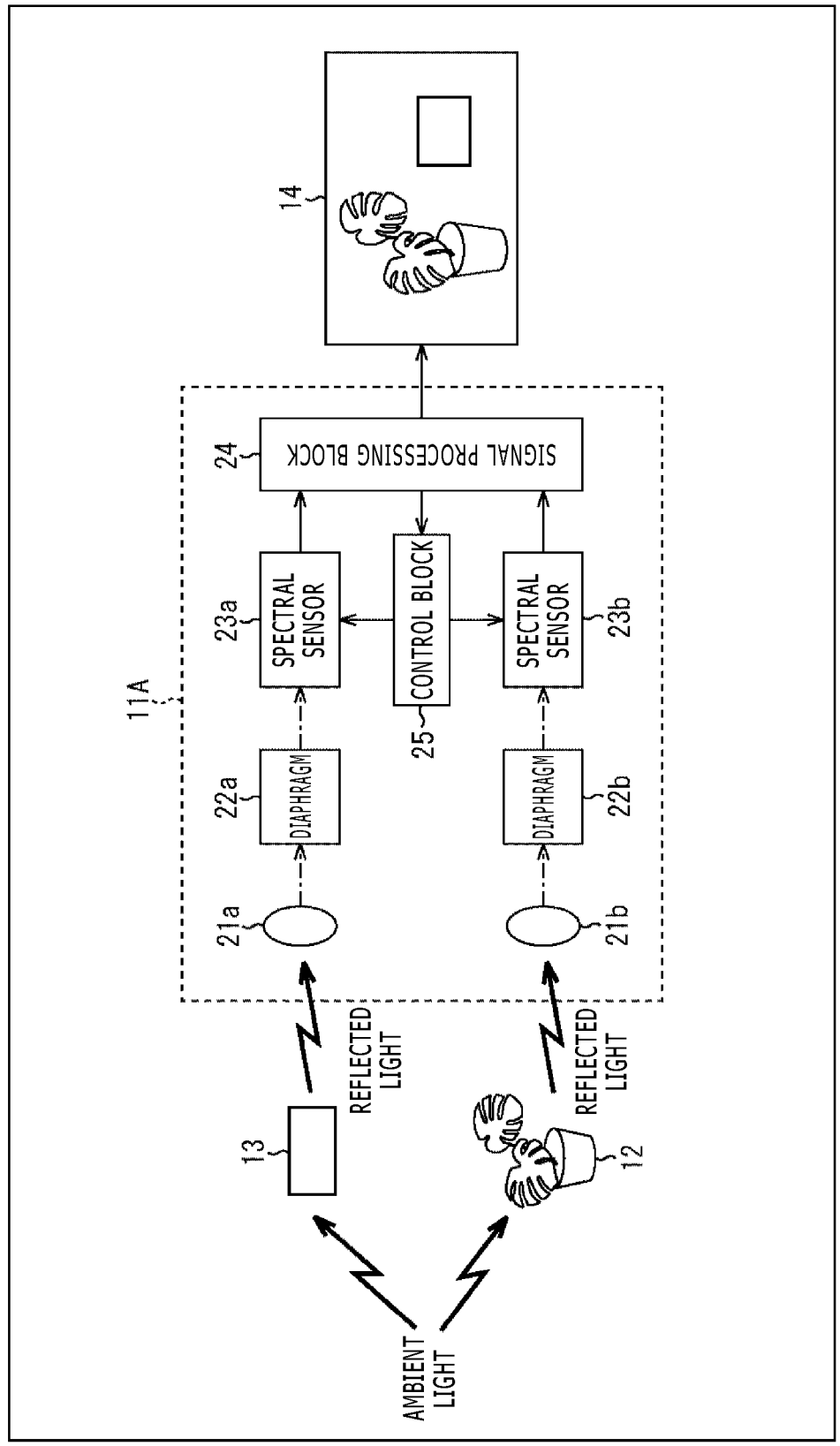
FIG. 22 is a block diagram illustrating an exemplary configuration of a second embodiment of the vegetation inspection apparatus to which the present technology is applied.

FIG. 22 is a block diagram illustrating an exemplary configuration of a second embodiment of the vegetation inspection apparatus to which the present technology is applied.

As illustrated in FIG. 22, a vegetation inspection apparatus 11A includes two optical systems 21a and 21b, two diaphragms 22a and 22b, two spectral sensors 23a and 23b, a signal processing block 24, and a control block 25. Elements of the vegetation inspection apparatus 11A illustrated in FIG. 22 that are identical with the corresponding elements of the vegetation inspection apparatus 11 illustrated in FIG. 1 are designated by the same reference symbols as their corresponding elements and will not be redundantly described in detail. In short, the vegetation inspection apparatus 11A differs from the vegetation inspection apparatus 11 illustrated in FIG. 1 in that the former includes two pieces each of the optical system 21, the diaphragm 22, and the spectral sensor 23.

The vegetation inspection apparatus 11A uses the optical system 21a, the diaphragm 22a, and the spectral sensor 23a to detect light reflected from the reference reflective plate 13, and uses the optical system 21b, the diaphragm 22b, and the spectral sensor 23b to detect light reflected from the inspection target 12. As mentioned above, the vegetation inspection apparatus 11A is configured so that the detection of light reflected from the reference reflective plate 13 is separate from the detection of light reflected from the inspection target 12.

In a case where, for example, the inspection target 12 and the reference reflective plate 13 differ in size, different zoom magnifications need to be set for sensing the inspection target 12 and the reference reflective plate 13 individually. Therefore, the vegetation inspection apparatus 11A is configured to be able to sense the inspection target 12 and the reference reflective plate 13 at appropriate different zoom magnifications.

Then, in the vegetation inspection apparatus 11A, the spectral sensor 23a outputs a detection signal of light reflected from the inspection target 12, and the spectral sensor 23b outputs a detection signal of the reference reflective plate 13. Thus, the spectral sensor 23a and the spectral sensor 23b enable the vegetation inspection apparatus 11A to properly control the sensitivity setting for each spectroscopic component. Therefore, the second red light R2 and second infrared light IR2 from the inspection target 12 and the reference reflective plate 13 can each easily be maintained within the dynamic range.

As a result, the vegetation inspection apparatus 11A is capable of inspecting the inspection target 12 with improved accuracy.

Third Embodiment of Vegetation Inspection Apparatus

Figure 23:
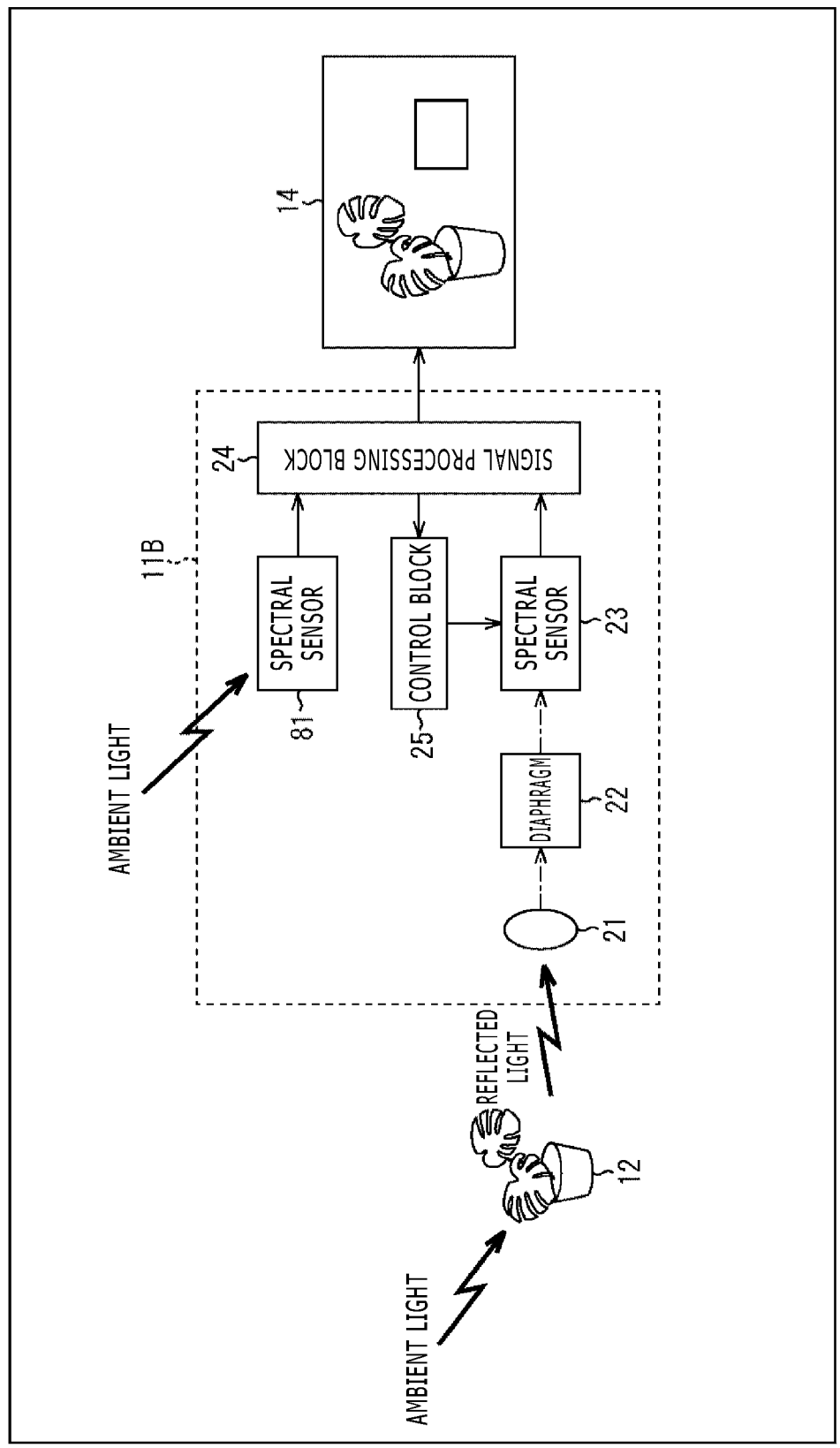
FIG. 23 is a block diagram illustrating an exemplary configuration of a third embodiment of the vegetation inspection apparatus to which the present technology is applied.

FIG. 23 is a block diagram illustrating an exemplary configuration of a third embodiment of the vegetation inspection apparatus to which the present technology is applied.

As illustrated in FIG. 23, a vegetation inspection apparatus 11B includes an optical system 21, a diaphragm 22, a spectral sensor 23, a signal processing block 24, a control block 25, and a spectral sensor 81. Elements of the vegetation inspection apparatus 11B illustrated in FIG. 23 that are identical with the corresponding elements of the vegetation inspection apparatus 11 illustrated in FIG. 1 are designated by the same reference symbols as their corresponding elements and will not be redundantly described in detail. In short, the vegetation inspection apparatus 11B differs from the vegetation inspection apparatus 11 illustrated in FIG. 1 in that the former includes the spectral sensor 81.

For example, while the inspection target 12 is irradiated with ambient light in the similar manner as descried earlier, the vegetation inspection apparatus 11B is capable of detecting the spectroscopic properties of the ambient light by using the spectral sensor 81 without using the reference reflective plate 13 in FIG. 1. More specifically, in the vegetation inspection apparatus 11B, the spectral sensor 81 receives the ambient light, detects its spectrum to generate a detection signal, supplies the detection signal to the signal processing block 24, and allows the signal processing block 24 to set the sensitivity to each spectroscopic component of the sensing element 32 (FIG. 1) in the spectral sensor 23. That is to say, the spectral sensor 81 does not indirectly detect the spectroscopic properties of the ambient light from light reflected from the reference reflective plate 13 depicted in FIG. 1, but detects the spectroscopic properties from the ambient light directly reaching the spectral sensor 81. It should be noted that, for example, a cover and a diffusion filter are installed over a sensor element in the spectral sensor 81. Therefore, the spectral sensor 81 detects the spectroscopic properties of the ambient light that is incident on the sensor element through, for example, the cover and the diffusion filter.

The vegetation inspection apparatus 11B having the above-described configuration is also capable of obtaining the earlier-described inspection results by setting the sensitivity of the spectral sensor 23 in the similar manner as described in conjunction with the sensitivity setup process, which is described earlier with reference to FIGS. 8 and 9.

Figure 24:
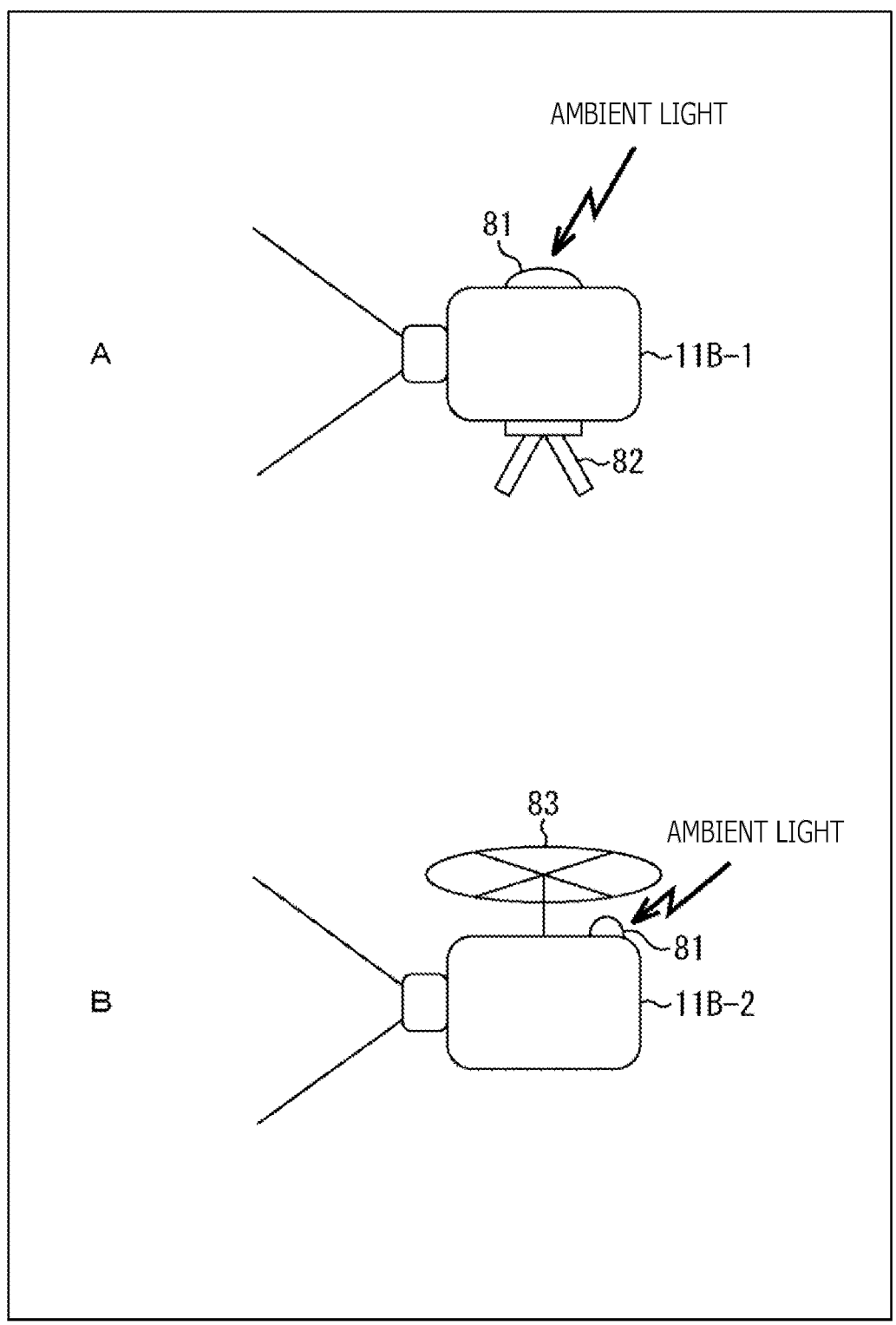
FIG. 24 is a diagram illustrating an exemplary configuration of the vegetation inspection apparatus for fixed-point observation and mobile observation.

Further, for example, as illustrated at A in FIG. 24, the vegetation inspection apparatus 11B can be used as a vegetation inspection apparatus 11B-1 that is mounted on a footing 82 to make fixed-point observations. Moreover, as illustrated at B in FIG. 24, the vegetation inspection apparatus 11B can be used as a vegetation inspection apparatus 11B-2 that is equipped with rotary wings 83 to make mobile observations, for example, as an unmanned aerial vehicle (UAV).

Figure 25:
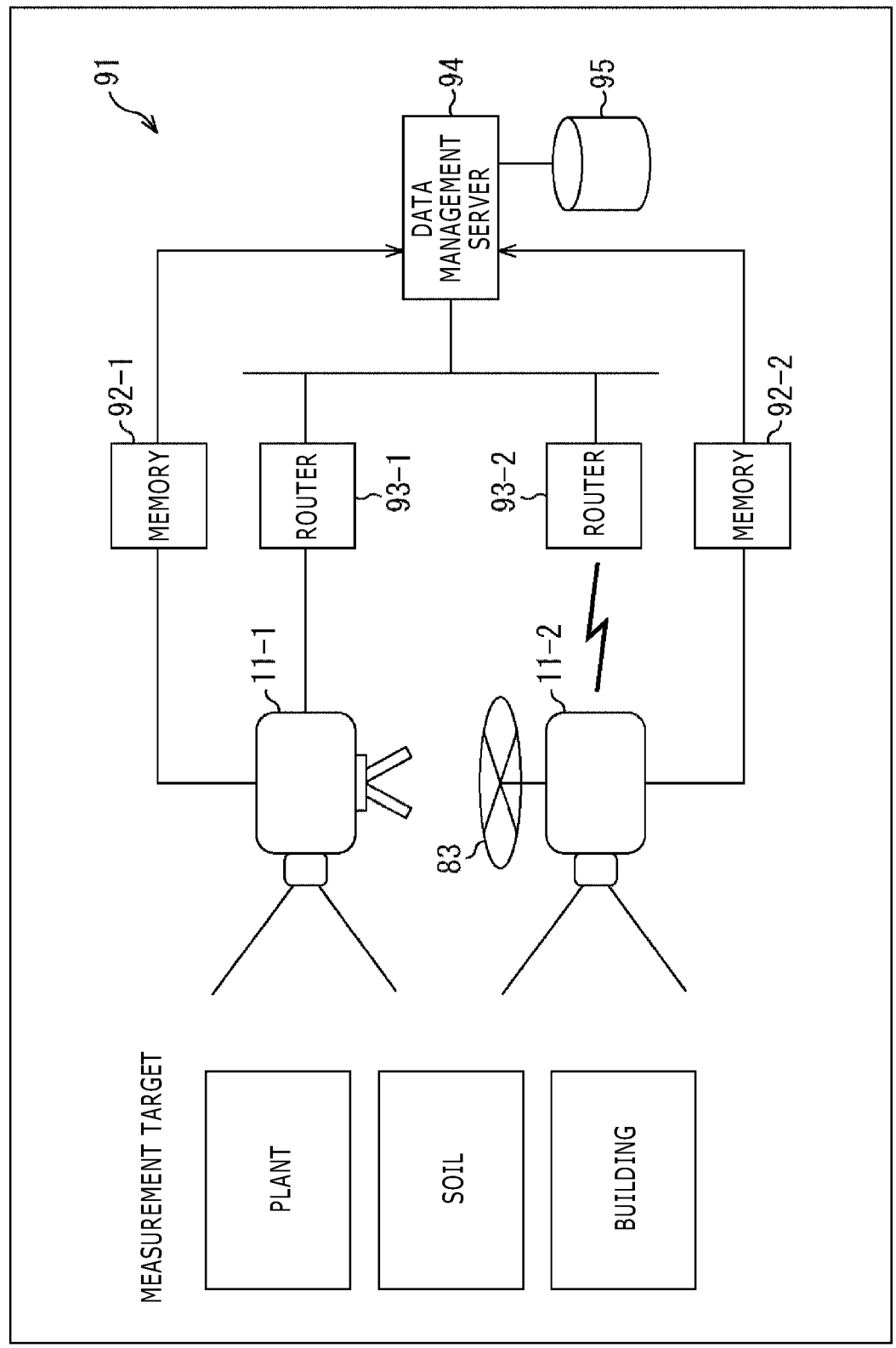
FIG. 25 is a diagram illustrating an exemplary overall configuration of a system that uses the vegetation inspection apparatus.

FIG. 25 is a diagram illustrating an exemplary overall configuration of a system that uses the vegetation inspection apparatus 11.

As illustrated in FIG. 25, an inspection system 91 is able, for example, to make fixed-point observations by using a vegetation inspection apparatus 11-1 installed at a fixed point and make mobile observations by using a vegetation inspection apparatus 11-2 equipped with rotary wings 83.

Further, in the inspection system 91, inspection data obtained by the vegetation inspection apparatus 11-1 can be collected off-line into a data management server 94 by using a memory 92-1, and collected into the data management server 94 over a wired network through a router 93-1. Similarly, inspection data obtained by the vegetation inspection apparatus 11-2 can be collected off-line into the data management server 94 by using a memory 92-2, and collected into the data management server 94 over the wired network through a router 93-2.

The data management server 94 is able to collect the inspection data from the vegetation inspection apparatuses 11-1 and 11-2 and store the collected inspection data in a recording section 95 so as to enable the inspection system 91 to make long-term observations. The inspection system 91 is not only capable of sensing vegetation by handling a plant as the inspection target as described earlier, but also capable of sensing, for example, soil or a building by handling it as the inspection target.

Furthermore, the inspection system 91 having the above configuration may alternatively be configured so that the vegetation inspection apparatuses 11-1 and 11-2 transmit spectroscopic components to the data management server 94 to let the data management server 94 set the sensitivity. That is to say, the process to be performed by the aforementioned signal processing block 24 may be performed by a certain block in the inspection system 91 instead of being performed in the vegetation inspection apparatuses 11-1 and 11-2.

According to an exemplary configuration depicted in FIG. 1, for example, the vegetation inspection apparatus 11 is configured so that the spectroscope 31 is disposed in the input stage of the sensing element 32 in the spectral sensor 23. However, the spectroscope 31 need not always be disposed immediately before the sensing element 32. For example, the vegetation inspection apparatus 11 may be configured so that the spectroscope 31 is disposed in the input stage of the diaphragm 22 or in the input stage of the optical system 21. Further, the vegetation inspection apparatus 11 may handle food as the inspection target 12. For example, the vegetation inspection apparatus 11 may be used to inspect a nutritional component (e.g., carotene) in food. Furthermore, the vegetation inspection apparatus 11 may be configured to control not only the sensitivity to red light R and infrared light IR, but also the sensitivity to blue light B or green light G. Moreover, for example, the vegetation inspection apparatus 11 may not only control the sensitivity with which the sensing element 32 detects reflected light, but also control the sensitivity of an element other than the sensing element 32.

Meanwhile, the spectroscope 31, which is configured as mentioned earlier so that an optical filter for transmitting a spectroscopic component is disposed for each pixel of the sensing element 32, may alternatively be configured so that a predetermined spectroscopic component is incident on each of a plurality of neighboring pixels, for example.

The processes described with reference to the flowcharts need not necessarily be performed chronologically in the order indicated in the flowcharts. Some of the processes may be performed in a parallel manner or on an individual basis (e.g., parallel processing or object-based processing). Further, a program may be processed by a single CPU or distributively processed by a plurality of CPUs.

Further, the above-described series of processes (information processing method) may be performed by hardware or by software. In a case where the series of processes is to be performed by software, the program forming the software is built in dedicated hardware of a computer, or installed on, for example, a general-purpose personal computer or other computer capable of executing various functions with various installed programs from a program recording medium storing the programs.

FIG. 26 is a block diagram illustrating an exemplary configuration of the hardware of a computer that executes the program to perform the above-described series of processes.

In the computer, a central processing unit (CPU) 101, a read-only memory (ROM) 102, and a random-access memory (RAM) 103 are interconnected by a bus 104.

The bus 104 is also connected to an input/output interface 105. The input/output interface 105 is connected to an input section 106, an output section 107, a storage section 108, a communication section 109, and a drive 110. The input section 106 includes a keyboard, a mouse, and a microphone. The output section 107 includes a display and a speaker. The storage section 108 includes a hard disk and a nonvolatile memory. The communication section 109 includes a network interface. The drive 110 is used to drive a removable recording medium 111 such as a magnetic disk, an optical disk, a magneto-optical disk, or a semiconductor memory.

In the computer configured as described, the CPU 101 loads the program, which is stored, for example, in the storage section 108, into the RAM 103 through the input/ output interface 105 and the bus 104, and executes the loaded program to perform the above-described series of processes.

The program to be executed by the computer (CPU 101) can be supplied after being recorded on a removable recording medium 111, which is a package medium such as, for example, a magnetic disk (including a flexible disk), an optical disc (e.g., a compact disc read-only memory (CD-ROM) or a digital versatile disc (DVD)), a magneto-optical disk, or a semiconductor memory. Alternatively, the program can be supplied through a wired or wireless transmission medium such as a local area network, the Internet, or a digital satellite broadcast.

The program can be installed in the storage section 108 through the input/output interface 105 when the removable recording medium 111 is inserted into the drive 110. Alternatively, the program can be received by the communication section 109 through a wired or wireless transmission medium and installed in the storage section 108. As another alternative, the program can be preinstalled in the ROM 102 or in the storage section 108.

The present technology may adopt the following configurations.

(1) An inspection apparatus including:
a detection section configured to detect a plurality of different wavelength region components of ambient light reflected from an inspection target to be inspected; and
a control section configured to control the sensitivity of each of the plurality of different wavelength region components.

(2) The inspection apparatus as described in (1) above, wherein the control section calculates an index to be used for the inspection of the inspection target by using particular ones of a plurality of spectroscopic components detected by the detection section.

(3) The inspection apparatus as described in (2) above, wherein the control section controls the sensitivity in such a manner that the level of detection by the detection section with respect to the particular spectroscopic components used to calculate the index to be used for the inspection of the inspection target is within a predetermined range.

(4) The inspection apparatus as described in (2) or (3) above, wherein the control section controls the sensitivity by calculating a histogram indicating the detection level in every wavelength region of light reflected from the inspection target that is detected by the detection section, and determining, on a basis of histograms of the particular spectroscopic components, whether or not the sensitivity is properly set for the detection section.

(5) The inspection apparatus as described in any one of (2) to (4) above, wherein the detection section further detects each of the spectroscopic components of the ambient light reflected from a reference object having known reflectance properties, and the control section calibrates the particular spectroscopic components by reference to the spectroscopic components of the light reflected from the reference object, the particular spectroscopic components being used to calculate the index to be used for the inspection of the inspection target.

(6) The inspection apparatus as described in (5) above, wherein the control section determines a calibration gain for making corrections such that the particular spectroscopic components of the light reflected from the reference object are at the same level, and corrects the particular spectroscopic components of the light reflected from the inspection target in accordance with the calibration gain.

(7) The inspection apparatus as described in any one of (1) to (6) above, wherein the detection section includes a sensing element having a plurality of planarly arrayed pixels, and
a spectroscope configured so that optical filters for transmitting the spectroscopic components are each disposed for each pixel of the sensing element.

(8) The inspection apparatus as described in (7) above, wherein the detection section includes
a beam splitter that splits light into a plurality of directions, and
a plurality of units of the spectroscope and of the sensing element that are disposed for respective directions into which the light is split by the beam splitter.

(9) The inspection apparatus as described in (7) or (8) above, wherein the spectroscope switches the spectroscopic components in a chronological order to disperse them, and
the sensing element performs a plurality of detection operations each time the spectroscope switches from one of the spectroscopic components to another.

(10) The inspection apparatus as described in any one of (5) to (9) above, wherein one unit of the detection section to detect light reflected from the inspection target and another unit of the detection section to detect light reflected from the reference object are individually provided.

(11) The inspection apparatus as described in any one of (1) to (10) above, further including:
an ambient light detection section configured to detect the ambient light.

(12) A sensing apparatus including:
a sensing element that detects, from each of planarly arrayed pixels, a plurality of different wavelength region components of ambient light reflected from an inspection target to be inspected; and
a control section configured to control the sensitivity of each of the different wavelength region components.

(13) A sensitivity control apparatus including:
a control section configured to control the sensitivity of each of a plurality of different wavelength region components of ambient light reflected from an inspection target to be inspected.

(14) An inspection method including:
detecting a plurality of different wavelength region components of ambient light reflected from an inspection target to be inspected; and
controlling the sensitivity of each of the different wavelength region components.

(15) A program causing a computer to function as:
a control section configured to control the sensitivity of each of a plurality of different wavelength region components of ambient light reflected from an inspection target to be inspected.

Embodiments of the present disclosure are not limited to the foregoing embodiments. The foregoing embodiments may be variously modified without departing from the spirit and scope of the present disclosure.

REFERENCE SIGNS LIST

11 Vegetation inspection apparatus
12 Inspection target
13 Reference reflective plate
14 Display section
21 Optical system
22 Diaphragm
23 Spectral sensor
24 Signal processing block 25 Control block
31 Spectroscope
32 Sensing element
41 Vertical scanning control circuit
42 Horizontal scanning control circuit
51 Pixel
52 Horizontal signal line
53 Vertical signal line
54 Switch
55 ADC
56 Output signal line
61 Photoelectric conversion section
62 Amplifier section
63 Switch
71 Beam splitter
72 Sensing apparatus
81 Spectral sensor
82 Footing
83 Rotary wings
91 Inspection system
92 Memory
93 Router
94 Data management server
95 Recording section

The invention claimed is:

1. An inspection apparatus comprising:
a reference plate:
an image detector configured to be disposed in opposition to the reference plate and an inspection target to be inspected, wherein the reference plate and the inspection target are in a field of view of the inspection apparatus, the image detector including a plurality of pixels configured to detect a plurality of different wavelength region components of a first portion of an ambient light reflected from the inspection target to be inspected and of a second portion of the ambient light reflected from the reference plate;
a memory storing program code; and
a processor that executes the program code to perform operations comprising
controlling a sensitivity of each of the plurality of pixels by calculating at least one histogram indicating a detection level by the image detector, and
determining, on a basis of respective histograms of particular ones of a plurality of spectroscopic components detected by the image detector, whether or not the sensitivity is properly set for the image detector.

2. The inspection apparatus according to claim 1, wherein the operations further comprise calculating an index to be used for the inspection of the inspection target by using the particular ones of the plurality of spectroscopic components.

3. The inspection apparatus according to claim 2, wherein the operations further comprise controlling the sensitivity in such a manner that the detection level with respect to the particular spectroscopic components is within a predetermined range, the particular spectroscopic components being used to calculate the index to be used for the inspection of the inspection target.

4. The inspection apparatus according to claim 3, wherein the operations further comprise calculating the respective histograms indicating the detection level in every wavelength region of the first portion of the ambient light reflected from the inspection target that is detected by the image detector.

5. The inspection apparatus according to claim 4, wherein the image detector further is configured to detect each of the spectroscopic components of the second portion of the ambient light reflected from the reference plate, the reference plate having known reflectance properties, and
the operations further comprise calibrating the particular spectroscopic components by reference to the spectroscopic components of the light reflected from the reference plate, the particular spectroscopic components being used to calculate the index to be used for the inspection of the inspection target.

6. The inspection apparatus according to claim 5, wherein the operations further comprise determining a calibration gain for making corrections such that the particular spectroscopic components of the second portion of the ambient light reflected from the reference plate are at the same level, and correcting the particular spectroscopic components of the first portion of the ambient light reflected from the inspection target in accordance with the calibration gain.

7. The inspection apparatus according to claim 1, wherein the plurality of pixels are arranged in a planar array, and the image detector includes a spectroscope configured so that optical filters for transmitting the spectroscopic components are each disposed for each pixel of the plurality of pixels.

8. The inspection apparatus according to claim 7, wherein the image detector includes
a beam splitter configured to split light into a predetermined number of directions, and
a predetermined number of units of the spectroscope and of the plurality of pixels that are disposed for respective directions into which the light is split by the beam splitter.

9. The inspection apparatus according to claim 7, wherein the spectroscope is configured to switch the spectroscopic components in a chronological order to disperse them, and
the operations further comprise performing a plurality of detection operations each time the spectroscope switches from one of the spectroscopic components to another.

10. The inspection apparatus according to claim 5, wherein one unit of the image detector is individually provided to detect the first portion of the ambient light reflected from the inspection target, and another unit of the image detector is individually provided to detect the second portion of the ambient light reflected from the reference object.

11. The inspection apparatus according to claim 1, further comprising:
an ambient light sensor configured to detect the ambient light.

12. A sensing apparatus comprising:
a reference plate:
an image detector configured to be disposed in opposition to the reference plate and an inspection target to be inspected, wherein the reference plate and the inspection target are in a field of view of the sensing apparatus, the image detector including pixels arranged in a planar array, the pixels configured to detect a plurality of different wavelength region components of a first portion of an ambient light reflected from the inspection target to be inspected and of a second portion of the ambient light reflected from the reference plate;
a memory storing program code; and
a processor that executes the program code to perform operations comprising
controlling a sensitivity of each of the pixels by calculating at least one histogram indicating a detection level by the image detector, and determining, on a basis of respective histograms of particular ones of a plurality of spectroscopic components detected by the image detector, whether or not the sensitivity is properly set for the image detector.

13. The inspection apparatus according to claim 1, wherein the image detector is configured to simultaneously detect the plurality of different wavelength region components of the first portion of the ambient light and of the second portion of the ambient light.

14. The inspection apparatus according to claim 1, wherein the image detector is configured to detect the plurality of different wavelength region components of the first portion of the ambient light and, subsequently, to detect the plurality of different wavelength region components of the second portion of the ambient light.

15. An inspection method for use in a sensing apparatus comprising a reference plate and an image detector, the image detector including pixels arranged in a planar array, the method comprising:
 disposing the image detector in opposition to the reference plate and an inspection target to be inspected, wherein the reference plate and the inspection target are in a field of view of the sensing apparatus;
 detecting, by the pixels, a plurality of different wavelength region components of a first portion of an ambient light reflected from the inspection target to be inspected and of a second portion of the ambient light reflected from the reference plate;
 controlling a sensitivity of each of the plurality of pixels by calculating at least one histogram indicating a detection level by an image detector including the plurality of pixels; and determining, on a basis of respective histograms of particular ones of a plurality of spectroscopic components detected by the image detector, whether or not the sensitivity is properly set for the image detector.

16. A non-transitory computer-readable medium storing program code for use in a sensing apparatus comprising a reference plate and an image detector, the program code being executable by a processor to perform operations comprising:
 disposing the image detector in opposition to the reference plate and an inspection target to be inspected, wherein the reference plate and the inspection target are in a field of view of the sensing apparatus;
 controlling a sensitivity of each the pixels by calculating at least one histogram indicating a detection level by an image detector including the plurality of pixels, the plurality of pixels configured to detect a plurality of different wavelength region components of a first portion of an ambient light reflected from the inspection target to be inspected and of a second portion of the ambient light reflected from the reference plate; and
 determining, on a basis of respective histograms of particular ones of a plurality of spectroscopic components detected by the image detector, whether or not the sensitivity is properly set for the image detector.

* * * * *